United States Patent
Lassalle et al.

(10) Patent No.: US 6,670,328 B1
(45) Date of Patent: Dec. 30, 2003

(54) PROTEINS AND PEPTIDES DERIVED FROM PROTEIN ESM-1 AND THEIR USES IN THE TREATMENT AND DIAGNOSIS OF DISEASES LINKED TO LEUKOCYTE MIGRATION

(75) Inventors: Phillippe Lassalle, Lille (FR); Genevieve Marchandise, Villeneuve d'Ascq (FR); Gwenola Kervoaze, Ronchin (FR); Andre Bernard Tonnel, Premesques (FR); Sophie Mollet, Lille (FR)

(73) Assignees: Institut Pasteur de Lille, Lille (FR); Institut National de la Sante et de la Recherche Medicale (INSERM), Paris (FR)

( * ) Notice: Subject to any disclaimer, the term of this patent is extended or adjusted under 35 U.S.C. 154(b) by 0 days.

(21) Appl. No.: 09/706,722

(22) Filed: Nov. 7, 2000

Related U.S. Application Data

(63) Continuation-in-part of application No. 09/102,909, filed on Jun. 23, 1998, now abandoned.
(60) Provisional application No. 60/050,614, filed on Jun. 24, 1997.

(51) Int. Cl.$^7$ .................. A61K 38/00; C07K 14/435
(52) U.S. Cl. .................. 514/12; 530/324; 530/350
(58) Field of Search .................. 530/350, 324; 514/12

(56) References Cited

U.S. PATENT DOCUMENTS 5,747,280 A * 5/1998 Hastings

FOREIGN PATENT DOCUMENTS

WO   WO/9617931   *   6/1996

OTHER PUBLICATIONS

Lasalle et al J. Biol. Chem. 271(34):20458–64.*
Lederman et al. Molecular Immunology, 28(11):1171–1181.*

* cited by examiner

*Primary Examiner*—Christina Chan
*Assistant Examiner*—F. Pierre VanderVegt
(74) *Attorney, Agent, or Firm*—Jacobson Holman PLLC

(57) ABSTRACT

Proteins and peptides derived from protein ESM-1 are used in the treatment and diagnosis of diseases linked to leukocyte migration.

2 Claims, 25 Drawing Sheets

```
                CTTCCCACCAGCAAAGACCACGACTGGAGAGCCGAGCCGGAGGCAGCTGGGAAAC              55
              ATGAAGAGCGTCTTGCTGCTGACCACGCTCCTCGTGCCTGCACACCTG                    103
                M  K  S  V  L  L  L  T  T  L  L  V  P  A  H  L     16
          GTGGCCGCCTGGAGCAATAATTATGCGGTGGACTGCCCTCAACACTGTGAC                    154
            V  A  A  W  S  N  N  Y  A  V  D  C  P  Q  H  C  D     33
          AGCAGTGAGTGCAAAAGCAGCCCGCGCTGCAAGAGGACAGTGCTCGACGAC                    205
            S  S  E  C  K  S  S  P  R  C  K  R  T  V  L  D  D     50
          TGTGGCTGCTGCCGAGTGTGCGCTGCAGGGCGGGGAGAAACTTGCTACCGC                    256
            C  G  C  C  R  V  C  A  A  G  R  G  E  T  C  Y  R     67
          ACAGTCTCAGGCATGGATGGCATGAAGTGTGGCCCGGGGCTGAGGTGTCAG                    307
            T  Y  S  G  M  D  G  M  K  C  G  P  G  L  R  C  Q     84
          CCTTCTAATGGGGAGGATCCTTTTGGTGAAGAGTTTGGTATCTGCAAAGAC                    358
            P  S  N  G  E  D  P  F  G  E  E  F  G  I  C  K  D    101
          TGTCCCTACGGCACCTTCGGGATGGATTGCAGAGAGACCTGCAACTGCCAG                    409
            C  P  Y  G  T  F  G  M  D  C  R  E  T  C  N  C  Q    118
          TCAGGCATCTGTGACAGGGGGACGGGAAAATGCCTGAAATTCCCCTTCTTC                    460
            S  G  I  C  D  R  G  T  G  K  C  L  K  F  P  F  F    135
          CAATATTCAGTAACCAAGTCTTCCAACAGATTTGTTTCTCTCACGGAGCAT                    511
            Q  Y  S  V  T  K  S  S  N  R  F  V  S  L  T  E  H    152
          GACATGGCATCTGGAGATGGCAATATTGTGAGAGAAGAAGTTGTGAAAGAG                    562
            D  M  A  S  G  D  G  N  I  V  R  E  E  V  V  K  E    169
          AATGCTGCCGGGTCTCCCGTAATGAGGAAATGGTTAAATCCACGCTGATCC                    613
            N  A  A  G  S  P  V  M  R  K  W  L  N  P  * * *      184
          CGGCTGTGATTTCTGAGAGAAGGCTCTATTTTCGTGATTGTTCAACACACAGCCAACATTT            674
          TAGGAACTTTCTAGATATAGCATAAGTACATGTAATTTTTGAAGATCCAAATTGTGATGCA            735
          TGGTGGATCCAGAAAACAAAAAGTAGGATACTTACAATCCATAACATCCATATGACTGAAC            796
          ACTTGTATGTGTTTGTTAAATATTCGAATGCATGTAGATTTGTTAAATGTGTGTGTATAGT            857
          AACACTGAAGAACTAAAAATGCAATTTAGGTAATCTTACATGGAGACAGGTCAACCAAAGA            918
          GGGAGCTAGGCAAAGCTGAAGACCGCAGTGAGTCAAATTAGTTCTTTGACTTTGATGTACA            979
          TTAATGTTGGGATATGGAATGAAGACTTAAGAGCAGGAGAAGATGGGGAGGGGGTGGGAGT           1040
          GGGAAATAAAATATTTAGCCCTTCCTTGGTAGGTAGCTTCTCTAGAATTTAATTGTGCTT            1100
          TTTTTTTTTTTTTGGCTTTGGGAAAAGTCAAAATAAAACAACCAGAAAACCCCTGAAGGA            1160
          AGTAAGATGTTTGAAGCTTATGGAAATTTGAGTAACAAACAGCTTTGAACTGAGAGCAATT           1221
          TCAAAAGGCTGCTGATGTAGTTCCCGGGTTACCTGTATCTGAAGGACGGTTCTGGGGCATA           1282
          GGAAACACATACACTTCCATAAATAGCTTTAACGTATGCCACCTCAGAGATAAATCTAAGA           1343
          AGTATTTTACCCACTGGTGGTTTGTGTGTGTATGAAGGTAAATATTTATATATTTTTATAA           1404
          ATAAATGTGTTAGTGCAAGTCATCTTCCCTACCCATATTTATCATCCTCTTGAGGAAAGA            1464
          AATCTAGTATTATTTGTTGAAAATGGTTAGAATAAAAACCTATGACTCTATAAGGTTTTC            1524
          AAACATCTGAGGCATGATAAATTTATTATCCATAATTATAGGAGTCACTCTGGATTTCAAA           1585
          AAATGTCAAAAAATGAGCAACAGAGGGACCTTATTTAAACATAAGTGCTGTGACTTCGGTG           1646
          AATTTTCAATTTAAGGTATGAAAATAAGTTTTTAGGAGGTTTGTAAAAGAAGAATCAATTT           1707
          TCAGCAGAAAACATGTCAACTTTAAAATATAGGTGGAATTAGGAGTATATTTGAAAGAATC           1768
          TTAGCACAAACAGGACTGTTGTACTAGATGTTCTTAGGAAATATCTCAGAAGTATTTTATT           1829
          TGAAGTGAAGAACTTATTTAAGAATTATTTCAGTATTTACCTGTATTTTATTCTTGAAGTT           1890
          GGCCAACAGAGTTGTGAATGTGTGTGGAAGGCCTTTGAATGTAAAGCTGCATAAGCTGTTA           1951
          GGTTTTGTTTTAAAAGGACATGTTTATTATTGTTCAATAAAAAAGAACAAGATAC  3'            2006
```

FIGURE 1B

```
ESM-1    19  A W S N N Y A V D C P Q H C D S S E C K - - S S P R C - - K R T V L D D
itb2    523  D V P N K K I Y G Q F C E C D T I N C E R Y N G Q V C G G P G R G L C F ESM-1    52  C G C C R V C A - - - A G R G E T C Y R T Y S G - - - M D G M K C G P G
itb2    559  C G K C R - C H P G F E G S A C Q C E R T E G C L N P R R V E C S G R ESM-1    81  L R C Q P S N G E D P F G E E F G I C K D C P Y G T F G M D C R E T C N
itb2    594  G R C R C N V C E C H S G Y Q L P L C Q E C P G C P S P C G K Y I S C A ESM-1   116  C Q S G I C D R G T G K C L K F P F F Q Y S V T K S S N R F V S L T E H
itb2    629  E C L K F E K G P F G K N C S A A C P G L Q L S N N P V K G R T C K E R ESM-1   152  D M A S G D G N I V R E E V V K E N A A G S P V M R K W L N P R
itb2    665  D S E G C W V A Y T L E Q Q D G M D R Y L I Y V D E S R E C V A G P N ESM-1    19  A W S N N Y A V D C P Q H C D S S E C K S S P R C - - K R T V L D D C G
fbn1     51  I C L D I R L E T C F L R Y E D E E C - T L P - - I A G R H R M D A C -

ESM-1    54  C C R V C A A G R G E T C - - - - Y R T Y S G M D G M K C - - G P G L R
fbn1     83  C C S V G A A W G T E C E E C P M R N T P E Y E E L - C P R G P G F A ESM-1    83  C Q P S N G E D P F G E E F G I C K D C P Y G T F G M D C R E T C N C Q
fbn1    106  T K E I T N G K P F F K D I N E C K M I P S L C T H G K C R N T I G S F ESM-1   119  S G I C D R G T G K C L K F P F F Q Y S V T K S S N R F V S L T E H D M
fbn1    154  K C R C D S G F A L D S E E R N C T D I D E C R I S P D L C G R G Q C V ESM-1   155  A S G D G N I V R E E V V K E N A A G S P V M R K W L N P R
fbn1    190  N T P G D F E C K C D E G Y E S G F A A A K N C M D I D E C Q R D ESM-1    19  A W S N N Y A V D C P Q H C D S S E C K S S P R C K R T V L D D C G C C
pca2     58  P C Q I C V C D N G A I L C D K I E C Q D V L D C A D P V T P P G E C C ESM-1    55  R V C A A G R G E T C Y R T Y S G M D G M K C G P G L R C Q P S N G E D
pca2     93  P V C S Q T P G G G N T N F G R R K G Q K G E P G L V P V V T G I R G ESM-1    91  P F G E E F G I C K D C P Y G T F G M D C R E T C N C Q S G I C D R G T
pca2    130  R P G P A G P P G S Q G P R G E R G P K G R P G R P G P Q G I D G E P G ESM-1   127  G K C L K F P F F Q Y S V T K S S N R F V S L T E H D M A S G D G N I V
pca2    165  V P G Q P G A P G P P G H P S H P G P D G L S R P F S A Q M A G L D E K ESM-1   163  R E E V V K E N A A G S P V M R K W L N P R
pca2    201  S G L G S Q V G L M P G S V G P V G P R G P Q G L ESM-1    19  A W S N N Y A V D C P Q H C D S S E C K S S P R C K R T V L D D C G C C
lmb2    775  A S S L V Y N G A L P C Q C D P Q G S L S S - E C N P H G - G Q C R C K ESM-1    56  R V C A A G R G E T C Y R T Y S G M D G M K C G P G L R C Q P S N G E D
lmb2    809  P G V V G R R C D A C A T G Y Y G F G P A G C Q A C - Q C S P D G A L S ESM-1    91  P F G E - E F G I C K D C P Y G T F G M D C R E T C N C Q S G I C D R G
lmb2    843  A L C E G T S G Q C L - C R T G A F G L R C - D H C Q R G Q W G F P N C ESM-1   126  T G K C L K F P F F Q Y S V T K S S N R F V S L T E H D M A S G D G N I
lmb2    876  R P C V N G R A D E C D A H T G A C L G C R D Y T G G E H C E R C I A ESM-1   162  V R E E V V K E N A A G S P V M R K W L N P R
lmb2    912  G F H G D P R L P Y G G Q C R P C P C P E G P G S Q
```

FIGURE 2

SEQUENCE LISTING

<160> NUMBER OF SEQ ID NOS: 10

<210> SEQ ID NO 1
<211> LENGTH: 2006
<212> TYPE: DNA
<213> ORGANISM: Homo sapiens
<220> FEATURE:
<221> NAME/KEY: CDS
<222> LOCATION: (56)..(607)

<400> SEQUENCE: 1

```
cttcccacca gcaaagacca cgactggaga gccgagccgg aggcagctgg gaaac atg      58
                                                              Met
                                                                1 aag agc gtc ttg ctg ctg acc acg ctc ctc gtg cct gca cac ctg gtg     106
Lys Ser Val Leu Leu Leu Thr Thr Leu Leu Val Pro Ala His Leu Val
              5                  10                  15 gcc gcc tgg agc aat aat tat gcg gtg gac tgc cct caa cac tgt gac     154
Ala Ala Trp Ser Asn Asn Tyr Ala Val Asp Cys Pro Gln His Cys Asp
         20                  25                  30 agc agt gag tgc aaa agc agc ccg cgc tgc aag agg aca gtg ctc gac     202
Ser Ser Glu Cys Lys Ser Ser Pro Arg Cys Lys Arg Thr Val Leu Asp
     35                  40                  45 gac tgt ggc tgc tgc cga gtg tgc gct gca ggg cgg gga gaa act tgc     250
Asp Cys Gly Cys Cys Arg Val Cys Ala Ala Gly Arg Gly Glu Thr Cys
 50                  55                  60                  65 tac cgc aca gtc tca ggc atg gat ggc atg aag tgt ggc ccg ggg ctg     298
Tyr Arg Thr Val Ser Gly Met Asp Gly Met Lys Cys Gly Pro Gly Leu
                 70                  75                  80 agg tgt cag cct tct aat ggg gag gat cct ttt ggt gaa gag ttt ggt     346
Arg Cys Gln Pro Ser Asn Gly Glu Asp Pro Phe Gly Glu Glu Phe Gly
             85                  90                  95 atc tgc aaa gac tgt ccc tac ggc acc ttc ggg atg gat tgc aga gag     394
Ile Cys Lys Asp Cys Pro Tyr Gly Thr Phe Gly Met Asp Cys Arg Glu
        100                 105                 110 acc tgc aac tgc cag tca ggc atc tgt gac agg ggg acg gga aaa tgc     442
Thr Cys Asn Cys Gln Ser Gly Ile Cys Asp Arg Gly Thr Gly Lys Cys
    115                 120                 125 ctg aaa ttc ccc ttc ttc caa tat tca gta acc aag tct tcc aac aga     490
Leu Lys Phe Pro Phe Phe Gln Tyr Ser Val Thr Lys Ser Ser Asn Arg
130                 135                 140                 145 ttt gtt tct ctc acg gag cat gac atg gca tct gga gat ggc aat att     538
Phe Val Ser Leu Thr Glu His Asp Met Ala Ser Gly Asp Gly Asn Ile
                150                 155                 160 gtg aga gaa gaa gtt gtg aaa gag aat gct gcc ggg tct ccc gta atg     586
Val Arg Glu Glu Val Val Lys Glu Asn Ala Ala Gly Ser Pro Val Met
            165                 170                 175 agg aaa tgg tta aat cca cgc    tgatcccggc tgtgatttct gagagaaggc     637
Arg Lys Trp Leu Asn Pro Arg
            180
```

-continued

```
tctattttcg tgattgttca acacacagcc aacattttag gaactttcta gatatagcat    697
aagtacatgt aattttttgaa gatccaaatt gtgatgcatg gtggatccag aaaacaaaaa   757
gtaggatact tacaatccat aacatccata tgactgaaca cttgtatgtg tttgttaaat    817
attcgaatgc atgtagattt gttaaatgtg tgtgtatagt aacactgaag aactaaaaat   877
gcaatttagg taatcttaca tggagacagg tcaaccaaag agggagctag caaagctga    937
agaccgcagt gagtcaaatt agttcttga ctttgatgta cattaatgtt gggatatgga    997
atgaagactt aagagcagga gaagatgggg agggggtggg agtgggaaat aaaatattta   1057
gccttcctt ggtaggtagc ttctctagaa tttaattgtg cttttttttt tttttggct     1117
ttgggaaaag tcaaataaa acaaccagaa accccctgaa ggaagtaaga tgtttgaagc    1177
ttatggaaat ttgagtaaca aacagctttg aactgagagc aatttcaaaa ggctgctgat   1237
gtagttcccg ggttacctgt atctgaagga cggttctggg gcataggaaa cacatacact   1297
tccataaata gctttaacgt atgccacctc agagataaat ctaagaagta ttttacccac   1357
tggtggtttg tgtgtgtatg aagtaaata tttatatatt tttataaata aatgtgttag    1417
tgcaagtcat cttccctacc catatttatc atcctcttga ggaaagaaat ctagtattat   1477
ttgttgaaaa tggttagaat aaaaacctat gactctataa ggttttcaaa catctgaggc   1537
atgataaatt tattatccat aattatagga gtcactctgg atttcaaaaa atgtcaaaaa   1597
acgagcaaca gagggacctt atttaaacat aagtgctgtg acttcggtga attttcaatt   1657
taaggtatga aaataagttt ttaggaggtt tgtaaaagaa gaatcaattt tcagcagaaa   1717
acatgtcaac tttaaaatat aggtggaatt aggagtatat ttgaaagaat cttagcacaa   1777
acaggactgt tgtactagat gttcttagga aatatctcag aagtattta tttgaagtga    1837
agaacttatt taagaattat ttcagtattt acctgtattt tattcttgaa gttggccaac   1897
agagttgtga atgtgtgtgg aaggccttg aatgtaaagc tgcataagct gttaggtttt    1957
gttttaaaag gacatgttta ttattgttca ataaaaaaga acaagatac                2006
```

<210> SEQ ID NO 2
<211> LENGTH: 184
<212> TYPE: PRT
<213> ORGANISM: Homo sapiens

<400> SEQUENCE: 2

```
Met Lys Ser Val Leu Leu Leu Thr Thr Leu Leu Val Pro Ala His Leu
 1               5                  10                  15

Val Ala Ala Trp Ser Asn Asn Tyr Ala Val Asp Cys Pro His Cys
                20                  25                  30

Asp Ser Ser Glu Cys Lys Ser Ser Pro Arg Cys Lys Arg Thr Val Leu
            35                  40                  45

Asp Asp Cys Gly Cys Cys Arg Val Cys Ala Ala Gly Arg Gly Glu Thr
        50                  55                  60

Cys Tyr Arg Thr Val Ser Gly Met Asp Gly Met Lys Cys Gly Pro Gly
 65                  70                  75                  80

Leu Arg Cys Gln Pro Ser Asn Gly Glu Asp Pro Phe Gly Glu Glu Phe
                85                  90                  95

Gly Ile Cys Lys Asp Cys Pro Tyr Gly Thr Phe Gly Met Asp Cys Arg
            100                 105                 110

Glu Thr Cys Asn Cys Gln Ser Gly Ile Cys Asp Arg Gly Thr Gly Lys
        115                 120                 125

Cys Leu Lys Phe Pro Phe Phe Gln Tyr Ser Val Thr Lys Ser Ser Asn
```

-continued

```
            130                 135                 140
Arg Phe Val Ser Leu Thr Glu His Asp Met Ala Ser Gly Asp Gly Asn
145                 150                 155                 160

Ile Val Arg Glu Val Val Lys Glu Asn Ala Ala Gly Ser Pro Val
                165                 170                 175

Met Arg Lys Trp Leu Asn Pro Arg
            180

<210> SEQ ID NO 3
<211> LENGTH: 165
<212> TYPE: PRT
<213> ORGANISM: Homo sapiens

<400> SEQUENCE: 3

Trp Ser Asn Asn Tyr Ala Val Asp Cys Pro Gln His Cys Asp Ser Ser
  1               5                  10                  15

Glu Cys Lys Ser Ser Pro Arg Cys Lys Arg Thr Val Leu Asp Asp Cys
             20                  25                  30

Gly Cys Cys Arg Val Cys Ala Ala Gly Arg Gly Glu Thr Cys Tyr Arg
         35                  40                  45

Thr Val Ser Gly Met Asp Gly Met Lys Cys Gly Pro Cys Leu Arg Cys
 50                  55                  60

Gln Pro Ser Asn Cys Glu Asp Pro Phe Gly Glu Phe Gly Ile Cys
 65                  70                  75                  80

Lys Asp Cys Pro Tyr Gly Thr Phe Gly Met Asp Cys Arg Glu Thr Cys
                 85                  90                  95

Asn Cys Gln Ser Cys Ile Cys Asp Arg Gly Thr Gly Lys Cys Leu Lys
            100                 105                 110

Phe Pro Phe Phe Gln Tyr Ser Val Thr Lys Ser Ser Asn Arg Phe Val
        115                 120                 125

Ser Leu Thr Glu His Asp Met Ala Ser Gly Asp Gly Asn Ile Val Arg
    130                 135                 140

Glu Glu Val Val Lys Glu Asn Ala Ala Gly Ser Pro Val Met Arg Lys
145                 150                 155                 160

Trp Leu Asn Pro Arg
                165

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 4
gttctttgac tttgatgt                                                   18

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 5
caactctgtt ggccaaact                                                  19

<210> SEQ ID NO 6
<211> LENGTH: 10
```

```
<212> TYPE: PRT
<213> ORGANISM: Homo sapiens

<400> SEQUENCE: 6

Trp Ser Ser Asn Asn Tyr Ala Val Asp Pro
 1               5                  10

<210> SEQ ID NO 7
<211> LENGTH: 178
<212> TYPE: PRT
<213> ORGANISM: Unknown Organism
<220> FEATURE:
<223> OTHER INFORMATION: Description of Unknown Organism: Integrin B2
      (itb2) amino acid sequence

<400> SEQUENCE: 7

Asp Val Pro Asn Lys Lys Ile Tyr Gly Gln Phe Cys Glu Cys Asp Thr
 1               5                  10                  15

Ile Asn Cys Glu Arg Tyr Asn Gly Gln Val Cys Gly Pro Gly Arg
            20                  25                  30

Gly Leu Cys Phe Cys Gly Lys Cys Arg Cys His Pro Gly Phe Glu Gly
            35                  40                  45

Ser Ala Cys Gln Cys Glu Arg Thr Thr Glu Gly Cys Leu Asn Pro Arg
    50                  55                  60

Arg Val Glu Cys Ser Gly Arg Gly Arg Cys Arg Cys Asn Val Cys Glu
65                  70                  75                  80

Cys His Ser Gly Tyr Gln Leu Pro Leu Cys Gln Glu Cys Pro Gly Cys
                85                  90                  95

Pro Ser Pro Cys Gly Lys Tyr Ile Ser Cys Ala Glu Cys Leu Lys Phe
            100                 105                 110

Glu Lys Gly Pro Phe Gly Lys Asn Cys Ser Ala Ala Cys Pro Gly Leu
        115                 120                 125

Gln Leu Ser Asn Asn Pro Val Lys Gly Arg Thr Cys Lys Glu Arg Asp
    130                 135                 140

Ser Glu Gly Cys Trp Val Ala Tyr Thr Leu Glu Gln Gln Asp Gly Met
145                 150                 155                 160

Asp Arg Tyr Leu Ile Tyr Val Asp Glu Ser Arg Glu Cys Val Ala Gly
                165                 170                 175

Pro Asn

<210> SEQ ID NO 8
<211> LENGTH: 172
<212> TYPE: PRT
<213> ORGANISM: Unknown Organism
<220> FEATURE:
<223> OTHER INFORMATION: Description of Unknown Organism: Fibrilin 1
      (fbn1) amino acid sequence

<400> SEQUENCE: 8

Ile Cys Leu Asp Ile Arg Leu Glu Thr Cys Phe Leu Arg Tyr Glu Asp
 1               5                  10                  15

Glu Glu Cys Thr Leu Pro Ile Ala Gly Arg His Arg Met Asp Ala Cys
            20                  25                  30

Cys Cys Ser Val Gly Ala Ala Trp Gly Thr Glu Glu Cys Glu Glu Cys
        35                  40                  45

Pro Met Arg Asn Thr Pro Glu Tyr Glu Leu Cys Pro Arg Gly Pro
    50                  55                  60

Gly Phe Ala Thr Lys Glu Ile Thr Asn Gly Lys Pro Phe Phe Lys Asp
65                  70                  75                  80
```

Ile Asn Glu Cys Lys Met Ile Pro Ser Leu Cys Thr His Gly Lys Cys
                85                  90                  95

Arg Asn Thr Ile Gly Ser Phe Lys Cys Arg Cys Asp Ser Gly Phe Ala
            100                 105                 110

Leu Asp Ser Glu Glu Arg Asn Cys Thr Asp Ile Asp Glu Cys Arg Ile
            115                 120                 125

Ser Pro Asp Leu Cys Gly Arg Gly Gln Cys Val Asn Thr Pro Gly Asp
        130                 135                 140

Phe Glu Cys Lys Cys Asp Glu Gly Tyr Glu Ser Gly Phe Ala Ala Ala
145                 150                 155                 160

Lys Asn Cys Met Asp Ile Asp Glu Cys Gln Arg Asp
                165                 170

<210> SEQ ID NO 9
<211> LENGTH: 169
<212> TYPE: PRT
<213> ORGANISM: Unknown Organism
<220> FEATURE:
<223> OTHER INFORMATION: Description of Unknown Organism: Procollagen a2
      (pca 2) amino acid sequence

<400> SEQUENCE: 9

Pro Cys Gln Ile Cys Val Cys Asp Asn Gly Ala Ile Leu Cys Asp Lys
1               5                   10                  15

Ile Glu Cys Gln Asp Val Leu Asp Cys Ala Asp Pro Val Thr Pro Pro
            20                  25                  30

Gly Glu Cys Cys Pro Val Cys Ser Gln Thr Pro Gly Gly Gly Asn Thr
        35                  40                  45

Asn Phe Gly Arg Gly Arg Lys Gly Gln Lys Gly Glu Pro Gly Leu Val
    50                  55                  60

Pro Val Val Thr Gly Ile Arg Gly Arg Pro Gly Pro Ala Gly Pro Pro
65                  70                  75                  80

Gly Ser Gln Gly Pro Arg Gly Glu Arg Gly Pro Lys Gly Arg Pro Gly
                85                  90                  95

Arg Pro Gly Pro Gln Gly Ile Asp Gly Glu Pro Gly Val Pro Gly Gln
            100                 105                 110

Pro Gly Ala Pro Gly Pro Pro Gly His Pro Ser His Pro Gly Pro Asp
            115                 120                 125

Gly Leu Ser Arg Pro Phe Ser Ala Gln Met Ala Gly Leu Asp Glu Lys
        130                 135                 140

Ser Gly Leu Gly Ser Gln Val Gly Leu Met Pro Gly Ser Val Gly Pro
145                 150                 155                 160

Val Gly Pro Arg Gly Pro Gln Gly Leu
                165

<210> SEQ ID NO 10
<211> LENGTH: 165
<212> TYPE: PRT
<213> ORGANISM: Unknown Organism
<220> FEATURE:
<223> OTHER INFORMATION: Description of Unknown Organism: Laminim B2
      (lmb2) amino acid sequence

<400> SEQUENCE: 10

Ala Ser Ser Leu Val Tyr Asn Gly Ala Leu Pro Cys Gln Cys Asp Pro
1               5                   10                  15

Gln Gly Ser Leu Ser Ser Glu Cys Asn Pro His Gly Gly Gln Cys Arg
            20                  25                  30

-continued

```
Cys Lys Pro Gly Val Val Gly Arg Arg Cys Asp Ala Cys Ala Thr Gly
        35                  40                  45

Tyr Tyr Gly Phe Gly Pro Ala Gly Cys Gln Ala Cys Gln Cys Ser Pro
    50                  55                  60

Asp Gly Ala Leu Ser Ala Leu Cys Glu Gly Thr Ser Gly Gln Cys Leu
65                  70                  75                  80

Cys Arg Thr Gly Ala Phe Gly Leu Arg Cys Asp His Cys Gln Arg Gly
                85                  90                  95

Gln Trp Gly Phe Pro Asn Cys Arg Pro Cys Val Cys Asn Gly Arg Ala
            100                 105                 110

Asp Glu Cys Asp Ala His Thr Gly Ala Cys Leu Gly Cys Arg Asp Tyr
        115                 120                 125

Thr Gly Gly Glu His Cys Glu Arg Cys Ile Ala Gly Phe His Gly Asp
    130                 135                 140

Pro Arg Leu Pro Tyr Gly Gly Gln Cys Arg Pro Cys Pro Cys Pro Glu
145                 150                 155                 160

Gly Pro Gly Ser Gln
                165
```

PROTEINS AND PEPTIDES DERIVED FROM PROTEIN ESM-1 AND THEIR USES IN THE TREATMENT AND DIAGNOSIS OF DISEASES LINKED TO LEUKOCYTE MIGRATION

This application is a continuation-in-part of Ser. No. 09/102,909, filed Jun. 23, 1998, now abandoned, which is a non-provisional application claiming the benefit of Provisional Application No. 60/050,614, filed Jun. 24, 1997. The entire disclosure of parent application Ser. No. 09/102,909 is incorporated herein by reference.

The present invention relates to proteins and peptides derived from a protein called Endothelial Cell Specific Molecule -1 (ESM-1).

It relates moreover to the use of such proteins and peptides in the treatment and diagnosis of diseases linked to leukocyte migration, and in particular to inflammatory diseases.

Positioned at the interface between circulating cells and tissues, the endothelial cells play a critical role in the homing and the local accumulation of leukocytes. Initial tethering and rolling, subsequent arrest and adhesion, and transendothelial migration constitute the current view of leukocyte migration. Leukocyte migration involves signal molecules, including selecting, chemoattractants, and integrins, which are present on endothelial cells. Their display of signals is carefully under the control of cytokines; E-selection, vascular cell adhesion molecule-1, IL-8; and RANTES (Regulated on Activation Normal T Cell Expressed) are expressed on endothelial cells only activated by cytokines, whereas ICAM-1, ICAM-2, AND IL-6, which are expressed constitutively in a low rate, are highly induced on endothelial cells in the presence of cytokines.

Vascular endothelium shows diversity among tissues, and there are fewer known mechanisms that regulate leukocyte migration and localization within specific tissues. E-selectin, GlyCAM-1, CD34, and MadCAM-1 contribute to the tissue-specific homing of circulating T-lymphocytes in skin, lymph nodes, and Peyer patches, respectively. GlyCAM-1, CD34, and MadCAM-1 are mucin-like carriers of selectin ligands. CD34 and MadCAM-1 are type 1 membrane glycoproteins, but GlyCAM-1 is secreted by the high endothelial veinules. In the other tissues, very little is known about the presence of such homing molecules on the endothelial cells. Therefore, identification of tissue- and endothelical cell-restricted molecules may contribute to a better understanding of these tissue specific leukocyte-endothelial cell interactions and to find some new method of therapy of diseases related with the leukocyte migration, in particular inflammatory diseases.

General Definitions of Biologically Relevant Terms

In accordance with the present invention there may be employed conventional molecular biology, microbiology, and recombinant DNA techniques within the skill of the art. Such techniques are explained fully in the literature. See, e.g., Sambrook et al., (1989); Glover, (1985); Gait, (1984); Hames and Higgins, (1985); Freshney, (1986); Perbal, (1984); and F. Ausubel et al., (1989).

Therefore, if appearing herein, the following terms shall have the definitions set out below.

The term "isolated" for the purposes of the present invention designates a biological material (nucleic acid or protein) which has been removed from its original environment (the environment in which it is naturally present).

For example, a polynucleotide present in the natural state in a plant or an animal is not isolated. The same polynucleotide separated from the adjacent nucleic acids in which it is naturally inserted in the genome of the plant or animal is considered as being "isolated".

Such a polynucleotide may be included in a vector and/or such a polynucleotide may be included in a composition and remains nevertheless in the isolated state because of the fact that the vector or the composition does not constitute its natural environment.

The term "purified" does not require the material to be present in a form exhibiting absolute purity, exclusive of the presence of other compounds. It is rather a relative definition.

A polynucleotide is in the "purified" state after purification of the starting material or of the natural material by at least one order of magnitude, preferably 2 or 3 and preferably 4 or 5 orders of magnitude.

For the purposes of the present description, the expression "nucleotide sequence" may be used to designate either a polynucleotide or a nucleic acid. The expression "nucleotide sequence" covers the genetic material itself and is therefore not restricted to the information relating to its sequence.

The terms "nucleic acid", "polynucleotide", "oligonucleotide" or "nucleotide sequence" cover RNA, DNA, gDNA or cDNA sequences or alternatively RNA/DNA hybrid sequences of more than one nucleotide, either in the single-stranded form or in the duplex, double-stranded form.

A "nucleic acid" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes cDNA, genomic DNA, synthetic DNA, and semi-synthetic DNA. The sequence of nucleotides that encodes a protein is called the sense sequence or coding sequence.

The term "nucleotide" designates both the natural nucleotides (A, T, G, C) as well as the modified nucleotides that comprise at least one modification such as (1) an analog of a purine, (2) an analog of a pyrimidine, or (3) an analogous sugar, examples of such modified nucleotides being described, for example, in the PCT application No. WO 95/04 064.

"Isolated polypeptide" or "isolated protein" is a polypeptide or protein which is substantially free of those compounds that are normally associated therewith in its natural state (e.g., other proteins or polypeptides, nucleic acids, carbohydrates, lipids). "Isolated" is not meant to exclude artificial or synthetic mixtures with other compounds, or the presence of impurities which do not interfere with biological activity, and which may be present, for example, due to incomplete purification, addition of stabilizers, or compounding into a pharmaceutically acceptable preparation.

Polypeptides of the invention include, but are not limited to, those containing, as a primary amino acid sequence, all or part of the amino acid sequence of a polypeptide of SEQ ID NO2 or SEQ ID NO3 according to the invention including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations are not expected to affect apparent molecular weight as determined by polyacrylamide gel electrophoresis, or isoelectric point.

Particularly Preferred Substitutions Are:

Lys for Arg and vice versa such that a positive charge may be maintained;
Glu for Asp and vice versa such that a negative charge may be maintained;
Ser for Thr such that a free —OH can be maintained; and
Gln for Asn such that a free $CONH_2$ can be maintained.

A "vector" is a replicon, such as plasmid, virus, phage or cosmid, to which another DNA segment-may be attached so as to bring about the replication of the attached segment. It is a circular or a linear DNA or RNA molecule which is either double-stranded or single-stranded. A "replicon" is any genetic element (e.g., plasmid, chromosome, virus) that functions as an autonomous unit of DNA replication in vivo, i.e., capable of replication under its own control.

Identity Between Two Nucleic Acid or Amino Acid Sequences

Identity refers to sequence identity between two peptides or between two nucleic acid molecules. Identity between sequences can be determined by comparing a position in each of the sequences which may be aligned for purposes of comparison. When a position in the compared sequences is occupied by the same base or amino acid, then the sequences are identical at that position. A degree of identity between nucleic acid sequences is a function of the number of identical nucleotides at positions shared by these sequences. A degree of identity between amino acid sequences is a function of the number of identical aminoacids at positions shared by these sequences. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for determining a comparison window may be conducted by the local homology algorithm of Smith and Waterman (1981), by the homology alignment algorithm of Needleman and Wunsch (1972), by the search for similarity method of Pearson and Lipman (1988), by computerized implementations of these algorithms (GAP, BESTFIT, FASTA, and TFASTA in the Wisconsin Genetics Solftware Package Release 7.0, Genetics. Computer Group, 575, Science Dr. Madison, Wis.), or by inspection. The best alignment (i.e., resulting in the highest percentage of identity over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g. A, T, C, G, U or I) occurs in both sequences to yield the number of matched positions, dividing the number of matched positions by the total number of positions in the window of comparison (i.e., the window size), and multiplying the result by 100 to yield the percentage of sequence identity.

Summary of the Invention

According to the invention, a polypeptide or a protein having at least 85% amino acid identity as regards a reference polypeptide or protein possesses preferably at least 90%, more preferably at least 95%, 96%, 97%, 98%, 99%, 99.5% and most preferably at least 99.7% amino acid identity as regards the reference polypeptide or protein.

In a most preferred embodiment, a polypeptide having at least 85% amino acid identity with an ESM-1 protein of SEQ ID n°2 or SEQ ID NO3 possesses the same biological properties or activities as regards the parent protein.

Most preferably, a protein having at least 85% amino acid identity with the secreted ESM-1 protein of SEQ ID NO3 possesses an ability to bind to the LFA-1 molecule of the same order of magnitude as the secreted ESM-1 protein itself. For example, a protein having at least 85%, 90%, 95%, 96%, 97%, 98%, 99%, 99.5% or 99.7% aminoacid identity with the secreted ESM-1 protein of SEQ ID NO3 is encompassed by the present invention if it binds to the LFA-1 molecule in a BIAcore system used in the experimental conditions disclosed in Example 10 with a dissociation constant comprised between 1 nM and 100 nM, advantageously between 1 nM and 50 nM, more preferably between 5 nM and 30 nM and most preferably between 8 nM and 25 nM.

It is therefore an object of the present invention to provide proteins and peptides which can be used in a method of therapy of diseases related with leukocyte migration.

It is another object of the present invention to provide S a method for determining the ESM-1 protein in biological samples.

In accomplishing these and other objects, there have been provided, in accordance with one aspect of the present invention, a protein the sequence of which shows an identity of at least 40, preferentially 60 or 70, and more preferentially 85% with a part of at least 25, 50, preferentially 70 aminoacids of the following sequence SEQ ID O 2.

Met Lys Ser Val Leu Leu Leu Thr Thr Leu Leu Val Pro Ala His Leu Val Ala Ala Trp Ser Asn Asn Tyr Ala Val Asp Cys Pro Gln His Cys Asp Ser Ser Glu Cys Lys Ser Ser Pro Arg Cys Lys Arg Thr Val Leu Asp Asp Cys Gly Cys Cys Arg Val Cys Ala Ala Gly Arg Gly Glu Thr Cys Tyr Arg Thr Val Ser Gly Met Asp Gly Met Lys Cys Gly Pro Gly Leu Arg Cys Gln Pro Ser Asn Gly Glu Asp Pro Phe Gly Glu Glu Phe Gly Ile Cys Lys Asp Cys Pro Tyr Gly Thr Phe Gly Met Asp Cys Arg Glu Thr Cys Asn Cys Gln Ser Gly Ile Cys Asp Arg Gly Thr Gly Lys Cys Leu Lys Phe Pro Phe Phe Gln Tyr Ser Val Thr Lys Ser Ser Asn Arg Phe Val Ser Leu Thr Glu His Asp Met Ala Ser Gly Asp Gly Asn Ile Val Arg Glu Glu Val Val Lys Glu Asn Ala Ala Gly Ser Pro Val Met Arg Lys Trp Leu Asn Pro Arg

Such a protein comprises preferentially between almost 40 and 200, more preferentially between almost 80 and 150 aminoacids.

Preferentially, at least a part of the sequence of this protein shows a similarity of at least 60, 75 and more preferentially 90% with a part of at least 50, preferentially 70 aminoacids of the sequence SEQ ID NO2.

Such a protein can show the following sequence SEQ ID NO 3.

Trp Ser Asn Asn Tyr Ala Val Asp Cys Pro Gln His Cys Asp Ser Ser Glu Cys Lys Ser Ser Pro Arg Cys Lys Arg Thr Val Leu Asp Asp Cys Gly Cys Cys Arg Val Cys Ala Ala Gly Arg Gly Glu Thr Cys Tyr Arg Thr Val Ser Gly Met Asp Gly Met Lys Cys Gly Pro Cys Leu Arg Cys Gln Pro Ser Asn Cys Glu Asp Pro Phe Gly Glu Glu Phe Gly Ile Cys Lys Asp Cys Pro Tyr Gly Thr Phe Gly Met Asp Cys Arg Glu Thr Cys Asn Cys Gln Ser Cys Ile Cys Asp Arg Gly Thr Gly Lys Cys Leu Lys Phe Pro Phe Phe Gln Tyr Ser Val Thr Lys Ser Ser Asn Arg Phe Val Ser Leu Thr Glu His Asp Met Ala Ser Gly Asp Gly Asn Ile Val Arg Glu Glu Val Val Lys Glu Asn Ala Ala Gly Ser Pro Val Met Arg Lys Trp Leu Asn Pro Arg

Another object of the present invention is a peptide composed of between almost 5 and 50 aminoacids and comprising an epitope, the said peptide showing at least a part of the sequence SEQ ID NO2. Such a peptide and proteins can be obtained by expressing oligonucleotides encoding them. Such oligonucleotides, which constitute other objects of the invention, can be mRNA or DNA, and in particular can be oligonucleotides comprising at least 50, preferentially 75 and more preferentially 150 nucleotides of the following sequence SEQ ID NO1.

CTTCCCACCA GCAAAGACCA CGACTGGAGA GCCGAGCCGG AGGCAGCTGG GAAAC ATG AAG AGC GTC TTG CTG CTG ACC ACG CTC CTC GTG CCT GCA CAC CTG GTG GCC GCC TGG AGC AAT AAT TAT GCG GTG GAC TGC CCT CAA CAC TGT GAC AGC AGT GAG TGC AAA AGC AGC CCG CGC TGC AAG AGG ACA GTG CTC GAC GAC TGT GGC TGC TGC CGA GTG TGC GCT GCA GGG CGG GGA GAA ACT TGC TAC CGC ACA GTC TCA GGC ATG GAT GGC ATG AAG TGT GGC CCG GGG CTG AGG TGT CAG CCT TCT AAT GGG GAG GAT CCT TTT GGT GAA GAG TTT GGT ATC TGC AAA GAC TGT CCC TAC GGC ACC TTC GGG ATG GAT TGC AGA GAG ACC TGC AAC TGC CAG TCA GGC ATC TGT GAC AGG GGG ACG GGA AAA TGC CTG AAA TTC CCC TTC TTC CAA TAT TCA GTA ACC AAG TCT TCC AAC AGA TTT GTT TCT CTC ACG GAG CAT GAC ATG GCA TCT GGA GAT GGC AAT ATT GTG AGA GAA GAA GTT GTG AAA GAG AAT GCT GCC GGG TCT CCC GTA ATG AGG AAA TGG TTA AAT CCA CGC T GATCCCGGCT GTGATTTCTG AGAGAAGGCTCTATTTTCGT ATTGTTCAA CACA-CAGCCA ACATTTTAGG AACTTTCTAG ATATAGCATA AGTACATGTA ATTTTTGAAG ATCCAAATTG TGATG-CATGG TGGATCCAGA AAACAAAAGTAGGATACTT ACAATCCATA ACATCCATAT GACTGAACAC TTG-TATGTGT TTGTTAAATATTCGAATGCA TGTA-GATTTG TTAAATGTGT GTGTATAGTA ACACT-GAAGA ACTAAAAATG CAATTTAGGT AATCTTACAT GGAGACAGGT CAACCAAAGA GGGAGCTAGG CAAAGCTGAA GACCGCAGTG AGTCAAATTA GTTCTTTGAC TTTGATGTAC ATTAATGTTG GGATATGGAA TGAAGACTTA AGAGCAGGAG AAGATGGGGA GGGGGTGGGA GTGGGAAATA AAATATTTAG CCCTTCCTTG GTAGGTAGCT TCTCTAGAAT TTAATTGTGC TTTTTTTTTT TTTTTG-GCTT TGGGAAAAGT CAAAATAAAA CAACCAGAAA ACCCCTGAAG GAAGTAAGAT GTTTGAAGCT TATG-GAAATT TGAGTAACAA ACAGCTTTGA ACT-GAGAGCA ATTTCAAAAG GCTGCTGATG TAGTTC-CCGG GTTACCTGTA TCTGAAGGAC GGTTCTGGGG CATAGGAAAC ACATACACTT CCATAAATAG CTT-TAACGTA TGCCACCTCA GAGATAAATC TAAGAAG-TAT TTTACCCACT GTGGTTTGT GTGTGTATGAAGG-TAAATAT TTATATATTT TTATAAATAA ATGTGTTAGT GCAAGTCATC TTCCCTACCC ATATTTATCA TCCTCT-TGAG GAAAGAAATC TAGTATTATT TGTTGAAAAT GGTTAGAATA AAAACCTATG ACTCTATAAG GTTTTCAAAC ATCTGAGGCA TGATAAATTT ATTATCCATA ATTATAGGAG TCACTCTGGA TTTCAAAAAA TGTCAAAAAA TGAGCAACAG AGG-GACCTTA TTTAAACATA AGTGCTGTGA CTTCGGT-GAA TTTTCAATTT AAGGTATGAA AATAAGTTTT TAGGAGGTTT GTAAAAGAAG AATCAATTTT CAG-CAGAAAA CATGTCAACT TTAAAATATA GGTG-GAATTA GGAGTATATT TGAAAGAATC TTAGCA-CAAA CAGGACTGTT GTACTAGATG TTCTTAGGAA ATATCTCAGA AGTATTTTAT TTGAAGTGAA GAACT-TATTT AAGAATTATT TCAGTATTTA CCTGTATTTT ATTCTTGAAG TTGGCCAACA GAGTTGTGAA TGT-GTGTGGA AGGCCTTTGA ATGTAAAGCT GCAT-AAGCTG TTAGGTTTTG TTTTAAAAGG ACATGTT-TAT TATTGTTCAA TAAAAAAGAA CAAGATAC

The proteins or the peptides can be produced by a method comprising:
introducing at least a part of sequence SEQ ID NO1 in an expression vector,
introducing the said vector in a suitable host cell, and
growing the said cell in conditions allowing the expression of the said protein.

The man skilled in the art is able to find without undue experiment which vector and which host cell will be suitable for the expression of the peptides and proteins according to the present invention.

In a preferred embodiment, the said peptides and proteins are produced by introducing a DNA sequence encoding for them according to the present invention, in the pcDNA3 vector. The pcDNA3 vector containing the said DNA is transfected in COS cells and these cells are grown in a suitable complete medium.

The peptides and proteins are recovered by methods which are known by the man skilled in the art.

For carrying out this method and the other embodiments described in the present application, the man skilled in the art may advantageously refer to the following manual: Sambrook et al. 1989, Molecular Cloning: A Laboratory Manual, Cold Spring Harbor ed. NEW YORK, or one of its more recent editions.

The inventors have shown that the expression of the nucleic acid sequence of SEQ ID O1 encoding ESM-1 in eukaryotic cells, such as endothelial cells and established cell lines transfected with a vector containing the nucleic acid sequence of SEQ ID NO1 led to the secretion of a ESM-1 protein lacking the 19 aminoacids of the signal peptide. Thus, the secreted ESM-1 protein was cleaved at the predicted site, leading to a mature ESM-1 polypeptide of 165 aminoacids having the aminoacid sequence of SEQ ID NO3.

The inventors have also shown that the secreted form of the ESM-1 protein having the aminoacid sequence of SEQ ID NO3 was able to bind to the cell-surface of human peripheral blood mononuclear cells (PBMC) as well as to the cell-surface of cells of the Jurkat cell line which is a B resting lymphoblastoid cell line. The binding of ESM-1 to the Jurkat cells was mostly dependent on the presence of divalent ions. This divalent ion-dependent binding of ESM-1 was found saturable, consistent with a receptor-like structure.

Further, co-immunoprecipitations demonstrated that ESM-1 was solely co-immunoprecipitated with anti-LFA-1 monoclonal antibodies.

The interaction between ESM-1 and LFA-1 was confirmed to be specific.

The interaction of LFA-1 and purified human secreted ESM-1 was examined using a BIAcore Biosensor System in order to monitor both the association and the dissociation between LFA-1 and ESM-1 in a real time. The measures of the rate constants demonstrated a physical interaction between ESM-1 and LFA-1 with a dissociation constant of 18.7 mM, close to that found between soluble ICAM-1 and LFA-1 of 60 nM. From the three LFA-1 monoclonal antibodies tested, two of them are neutralizing, but neither of them was able to inhibit ESM-1 binding. The inventors believe that there was no direct relationship between ESM-1 and the neutralizing activity of LFA-1 monoclonal antibodies, and that the ESM-1 binding site was not close to the sites involved in LFA-1/ICAM-1 interactions, namely the I domain.

In contrast to ICAM-1, the binding of ESM-1 to the Jurkat cells was higher at 4° C. than at 37° C. Further, the results of ESM-1 binding by various cell lines induced by PMA suggest that the ESM-1 binding site within the LFA-1 molecule is regulated and that among the different conformational or states which occur during the time course of LFA-1 activation, one of the earliest activation state of the LFA-1 molecule should include up-regulation of the ESM-1 binding site.

The inventors results also showed that ESM-1 reduced significantly the binding of soluble 3D-ICAM-1/Fc to Jurkat cells. Inversely, the soluble 3D-ICAM-1/Fc was shown to reduce to binding of ESM-1 to Jurkat cells. These results show that ESM-1 and ICAM-1 compete for the binding to the LFA-1.

Thus, the inventors have shown that the proteoglycan ESM-1, which is secreted by endothelial cells, interacts with LFA-1 and may influence directly LFA-1 function on human Jurkat cell line and also on circulating human lymphocytes and monocytes. ESM-1 is thus implicated in the regulation of leukocyte extravasation at the inflammatory sites, because of the essential role of the ICAM-1/LFA-1 interactions during firm adhesion.

In addition, ESM-1 might modulate the LFA-1/ICAM-1 costimulatory pathway and orientate the Th1/Th2 balance of the immune response, as it has been reported for anti-ICAM-1 and anti-LFA-1 blocking monoclonal antibodies (Zuckerman et al., 1998. Salomon et al., 1998).

In addition, a modification of the circulating level of ESM-1 has been shown in a population of mixed pulmonary of systemic septic patients. In all the groups of patients, the mean value of ESM-1 was highly elevated compared to healthy subjects. This increase in circulating ESM-1 was correlated with the level of clinical illness severity. Highest levels of circulating ESM-1 at the early stage of the disease were associated with a lower probability of survival after ten days.

Further, previous blood markers of sepsis such as CRP, procalcitonin and soluble ICAM-1 were not able to predict the prognosis of death, in contrast to the values obtained for circulating ESM-1. The fact that ESM-1 concentrations in blood can attain more than 100 ng/mL in patients with septic shock, it can be speculated that ESM-1 may have a potent in vivo regulatory activity on ICAM-1 and LFA-1-mediated functions. Thus, ESM-1, and more particularly the secreted form of ESM-1 having the aminoacid sequence of SEQ ID NO3 may be considered as a novel class of natural endothelial cell-derived molecule able to regulate LFA-1/ICAM-1 interactions and probably LFA-1 mediated functions. Thus, ESM-1 is implicated in the regulation of the LFA-1/ICAM-1 pathway and influence the recruitment of circulating lymphocytes to sites of inflammation as well as LFA-1 dependent leukocyte activation.

The peptides and proteins according to the present invention can be used in a method for the therapy of mammalian organisms of diseases linked to the leukocyte migration, wherein the said organisms are treated with these proteins or peptides. In a preferred embodiment, these peptides and proteins can be used in a method for the therapy of inflammatory diseases, in particular those which are chronic.

Such a method can be carried out by administering the said peptides or proteins to mammalian organisms, including man, the said peptides and proteins being in the form of compositions containing a suitable dose of the said peptides and proteins, as well as pharmacologically acceptable excipients.

The compositions containing peptides and proteins as described hereabove constitute other objects of the present invention.

Diseases which can be treated by the method according to the present invention can be in a general manner those which are linked with leukocyte migration, and in particular asthma, inflammatory reaction during sepsis, rhumatoid, vasculitis, or allogenic or xenogenic rejection during transplantation.

The present invention moreover relates to a method of diagnosis of diseases linked to leukocyte migration comprising the following steps:

bringing in contact the sample of the said organism with a protein or a peptide as described hereabove, and determining the antibody-antigen complexes which are formed.

A further object of the present invention is a method for determining anti-ESM-1 antibodies in a biological sample of an organism comprising the following steps:

bringing in contact a biological sample of an organism with a protein or a peptide as described hereabove, and determining the complexes which are formed.

The present invention moreover relates to kits for carrying out the said methods comprising at least one of the peptides or proteins as described hereabove.

Brief Description of the Drawings

The drawings of which a brief description is given hereunder illustrate the present invention.

FIG. 1B is the nucleotide (SEQ ID NO: 1) and predicted amino acid sequence (SEQ ID NO: 2) of ESM-1. Double underline indicates putative signal sequence. The mRNA decay consensus sequence motifs are underlined and potential polyadenylation sites are in bold type.

FIG. 2 is a comparison of the sequence of ESM-1 to amino acid sequences of several proteins. Shown is alignment of sequences computerized by the FASTA program. The ESM-1 sequence (residues 19–184 of SEQ ID NO: 2) is shown in the first line and compared with integrin β2

(itb2) (SEQ ID NO: 7), fibrilin 1 (fbn1) (SEQ ID NO: 8), procollagen α2 (pca 2) (SEQ ID NO: 9), and laminim β2 (lmb2) (SEQ ID NO: 10). Amino acid identity is boxed.

Figure 3A:
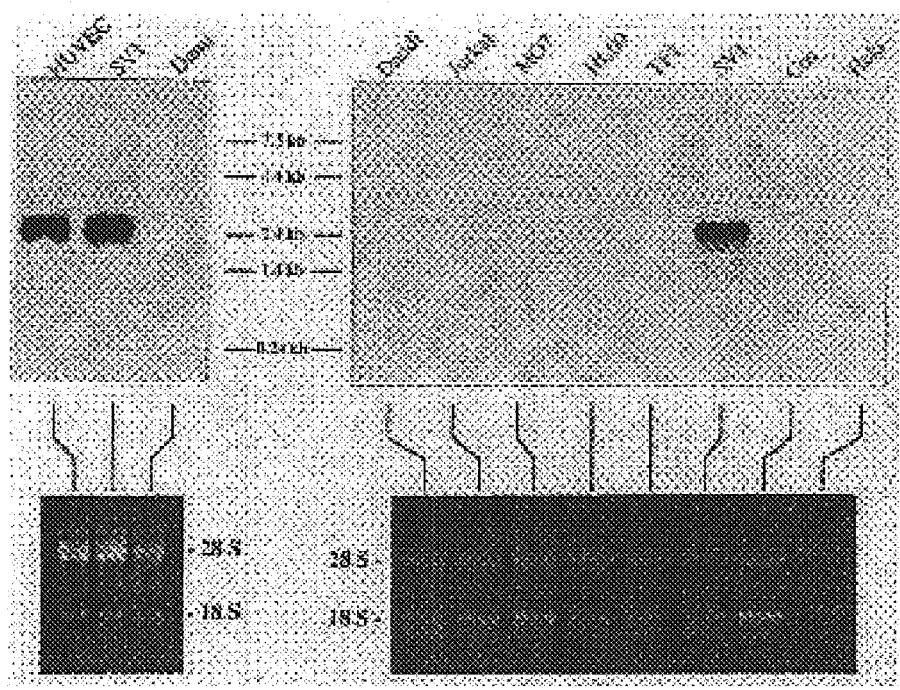
Figure 3B:
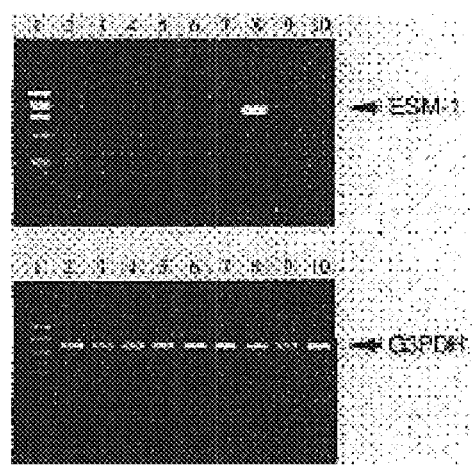

FIGS. 3A and 3B show the cellular distribution of ESM-1. FIG. 3A represents a multiple-cell Northern blot. 30 µg of total RNA were applied per lane. The Northern blots were sequentially hybridized with two ESM-1 probes, including the whole cDNA sequence of ESM-1.

FIG. 3B is a reverse transcriptase-PCR (RT-PCR) detection of ESM-1 transcripts in various human cell lines. Lane 1, 1,6 µg φX174 replicative form DNA/HaeIII fragments lane 2, Dami; lane 3, Daudi; lane 4, Jurkat; lane 5, MO7; lane 6, HL60, Lane 7, TF1; lane 8, HUVEC; lane 9, COS; lane 10, HeLa.

Figure 4:
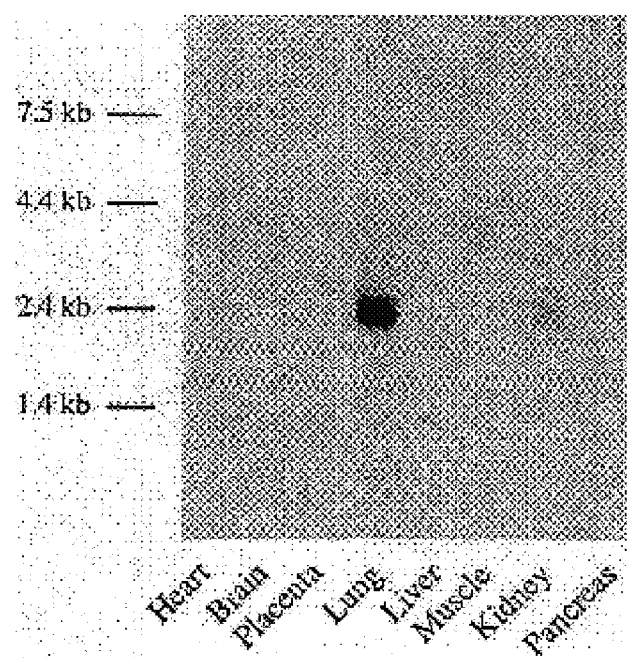

FIG. 4 represents the tissue distribution of ESM-1. Multiple human tissue Northern blot was purchased from Clontech.

Figure 5:
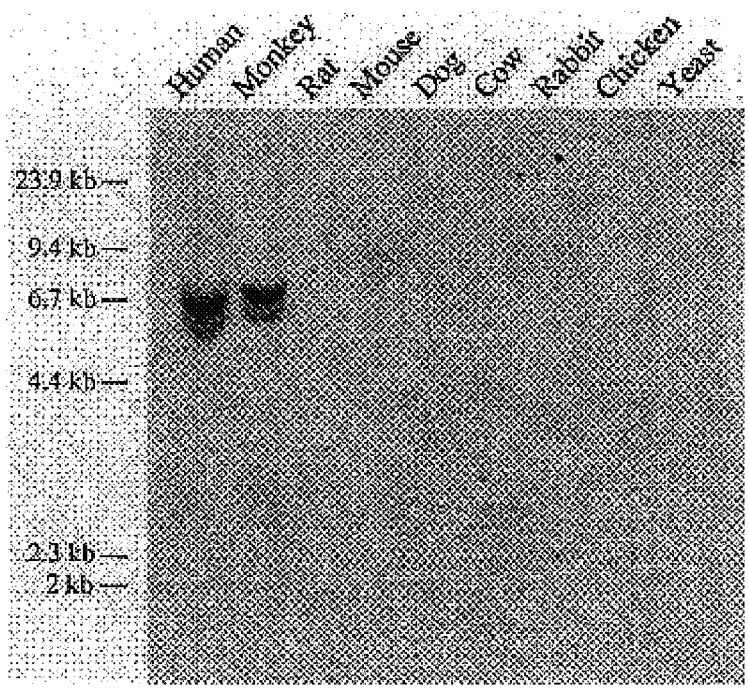

FIG. 5 is a Southern blot analysis of ESM-1 gene. The Zoo-blot (Clontech) was hybridized with the Hindill fragment of ESM-1 cDNA including the coding sequence of ESM-1.

Figure 6A:
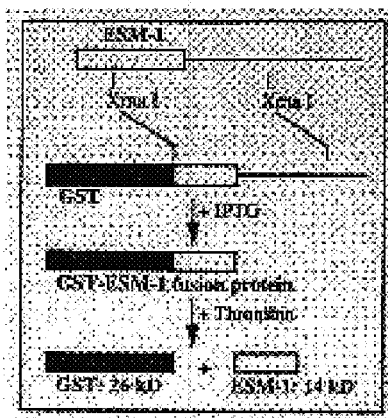

FIG. 6A represents construction, production, and purification scheme of the 14 kDa COOH-terminal ESM-1 polypeptide. The XmaI-digested fragment of ESM-1 was ligated into the XmaI-digested and calf intestine alkaline phosphatase-treated pGEX-2TK vector.

Figure 6B:
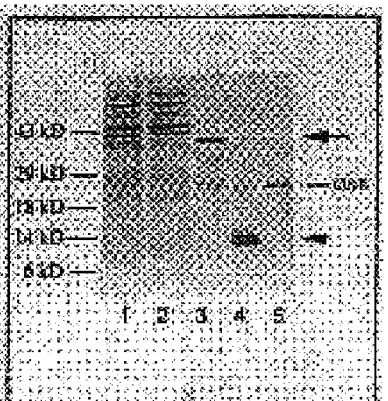

FIG. 6B is a SDS-PAGE analysis of ESM-1 protein product. Here is shown a 15% SDS-PAGE stained with Coomassie Brilliant Blue. Lanes 1 and 2, cleared bacterial lysate before (lane 1) and after (lane 2) passage through a glutathione-Sepharose 4B column, lane 3, gluthathione S-transferase fusion protein eluted with 5 mM glutathione in Tris-HCl (pH 8); lane 4, purified COOH- terminal ESM-1 polypeptide cleaved by thrombin; lane 5, glutathione eluate from the column after thrombin treatment. Arrow indicates the presence of glutathione S-transferase-ESM-1 fusion protein.

Figure 6C:
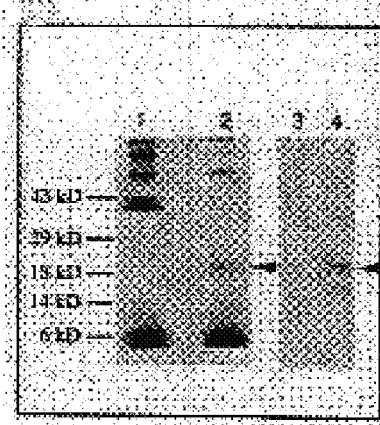

FIG. 6C represents ESM-1 expression in Sf9 cells. Lanes 1 and 2, SDS-PAGE analysis of metabolically labeled SF9 cells expressing ESM-1. Twenty microliters of crude supernatants were run in 15% SDS-PAGE. Lane 1, Sf9 cells; lane 2, Sf9 cells infected with ESM-1 recombinant baculovirus; lanes 3 and 4, Western blotting of Sf9 cell supernatants expressing ESM-1. Supernatants from Sf9 were 10×concentrated and 10 µl of each were run in 15% SDS-PGE and transferred onto an immobilon membrane (Amersham Corp.). The blots were probed with rabbit antiserum against ESM-1. Lane 3 Sf9 cells infected with hIL-5 recombinant baculovirus; lane 4, Sf9 cells expressing ESM-1.

Figure 6D:
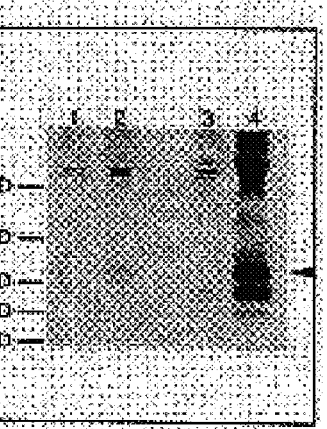

FIG. 6D represents ESM-1 expression in COS cells. ESM-1 and mock transfectants were metabolically labeled for 6 h at the second day after transfection. COS cell supernatants and COS cell lysates were incubated first with 5 µl of rabbit antiserum and second with protein A-Sepharose CL-4B. After extensive washing, the beads were boiled in Laemmli buffer containing β-mercaptoethanol. Twenty microliters were run in 15% SDS-PAGE, dried, and autoradiographed. Immunoprecipitates from COS cell supernatants are shown in lane 1 (mock transfected) and in lane 2 (ESM-1 transfected). Those from COS cell lysates are shown in lane 3 (mock transfected) and in lane 4 (ESM transfected).

Figures 7A, 7B:
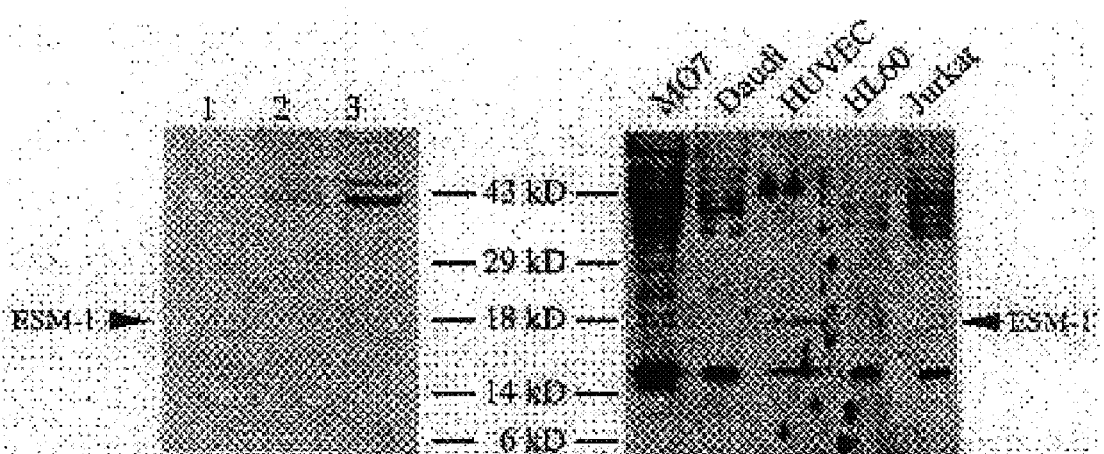

FIG. 7A illsutrates the detection of the ESM-1 protein in human umbilical vein endothelial cell (HUVEC). Immunoprecipitation of [$^{35}$S] methionine-labeled HUVECs. HUVECs ($10^6$) were overnight labeled with [$^{35}$S] methionine. The cell supernatant and the cell lysate were precleared with 5 µl of control rabbit serum and 50 µl of protein A-Sepharose for 2 h at 4° C. The cleared cell supernatant and cell lystate were then processed for immunoprecipitation as described for COS cells. Lane 1, HUVEC supernatant alone; lane 2, HUVEC supernatant incubated with 5 µl of rabbit anti-ESM-1 antiserum; lane 3, HUVEC lysate incubated with 5 µl of rabbit anti-ESM-1 antiserum.

FIG. 7B is a Western Blot analysis of HUVEC lysate. Ten microliters of various cell lysates were analyzed in Western blot. The membrane was probed with rabbit anti-ESM-1 antiserum. After several washings, bound antibodies were labeled by a peroxidase-conjugated goat antirabbit immunoglobulin and revealed by ECL.

Figures 8A, 8B, 8C:
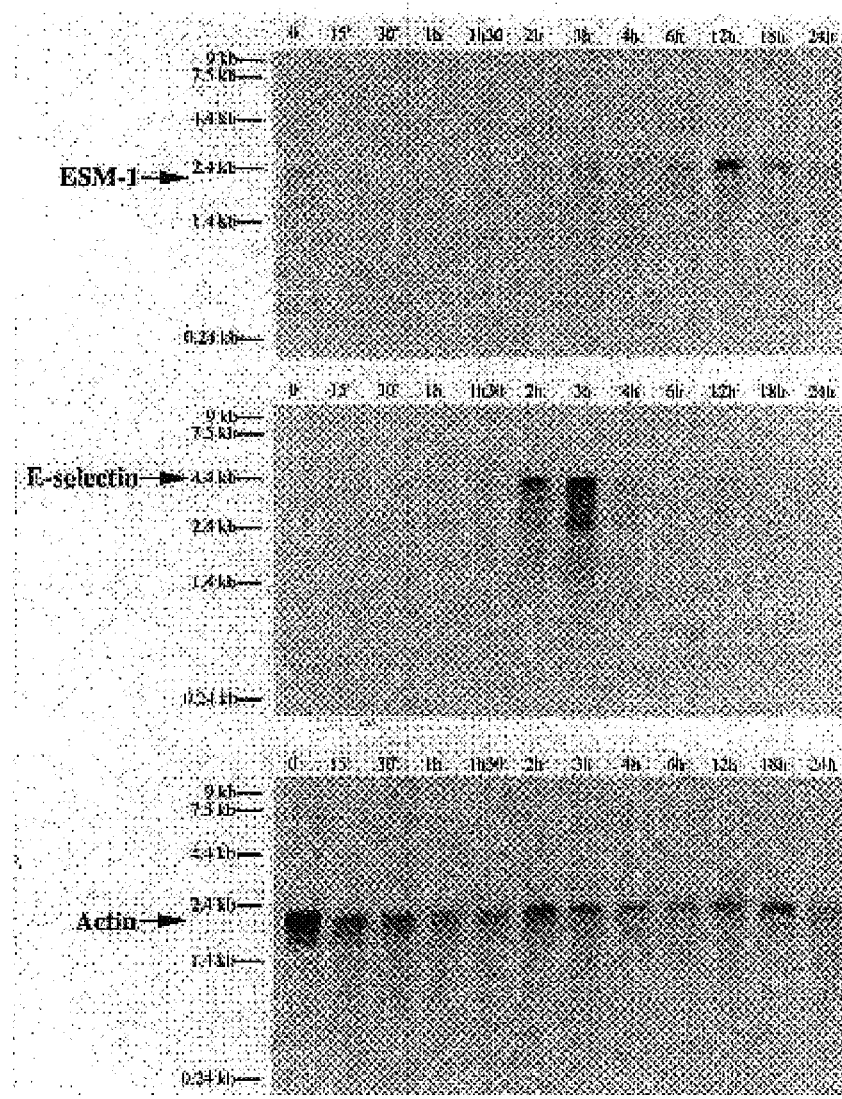

FIGS. 8 A–C illustrate the kinetic of TNFα-dependent ESM-1 gene up-regulation. HUVECs were cultured as described. TNFα(200 units/ml) was added to the culture medium. At different times the medium was removed and the cells were lysed in 4 M guanidine thiocyanate buffer. Total RNA was purified and separated in 1% formaldehyde agarose gel. The membranes were hydrizied first with an ESM-1 probe (HindIII DNA fragment) (FIG. 8A), second with an E-selection probe (PstI-EcoRI DNA fragment (FIG. 8B) and third with a β-actin probe (purchased from Clontech) (FIG. 8c).

Figures 9A, 9B, 9C:
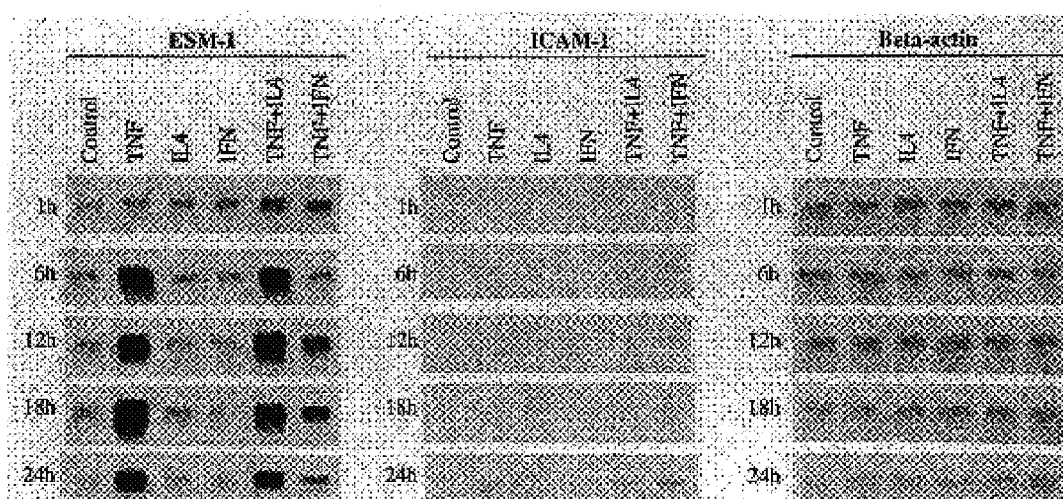

FIGS. 9 A–C illustrate the ESM-1 gene regulation by cytokines. Northern blot analysis of HUVECs stimulated with TNFα, IL-4, IFNY, TNFα+IL-4, and TNFα+IFNY, HUVECs were cultured as described. Cytokines were added and RNA were recovered at 1, 6, 18 and 24 h. Total RNA was electrophoresed and transferred. The membranes were hybridized first with a ESM-1 probe (HindIII DNA fragment) (FIG. 9A) second with an intercellular adhesion molecule 1 (ICAM-1) probe (EcoRI-XhoI DNA fragment FIG. 9B) and third with a β-actin probe (FIG. 9c).

Figure 10:
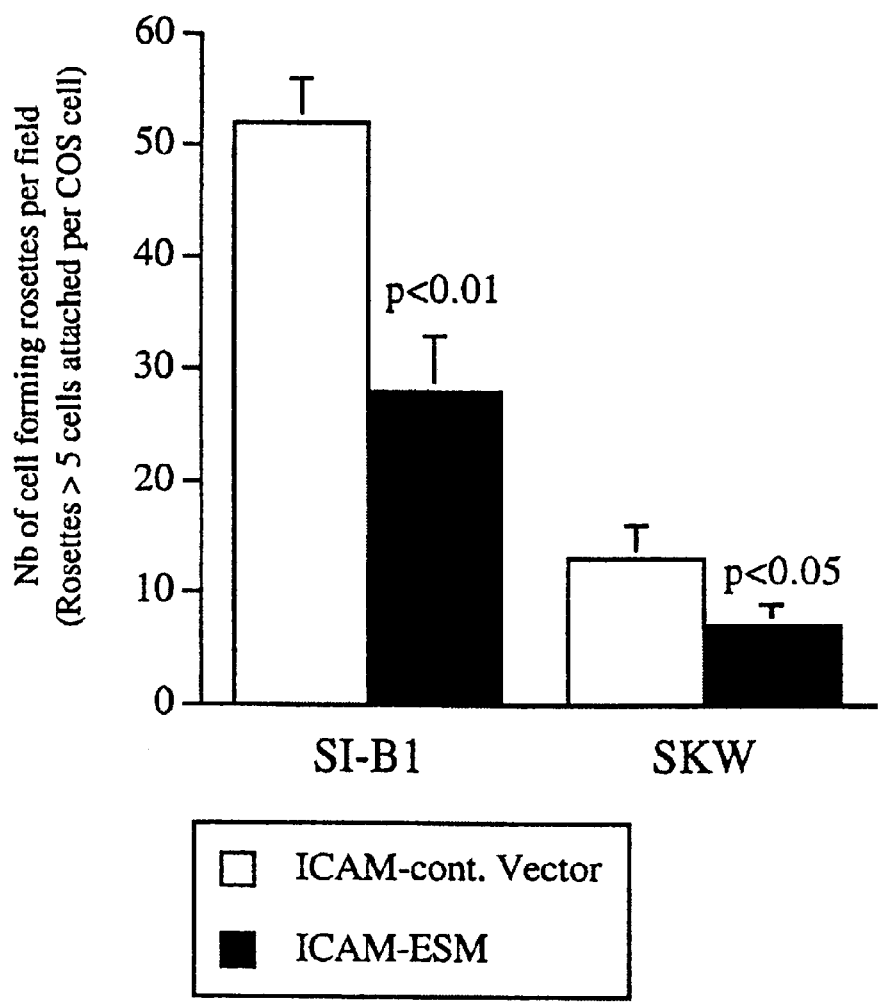

FIG. 10 illustrates the inhibition of ICAM-1 dependent intercellular adhesion by ESM-1 in Sl-B1 and SKW human cell lines.

Figure 11:
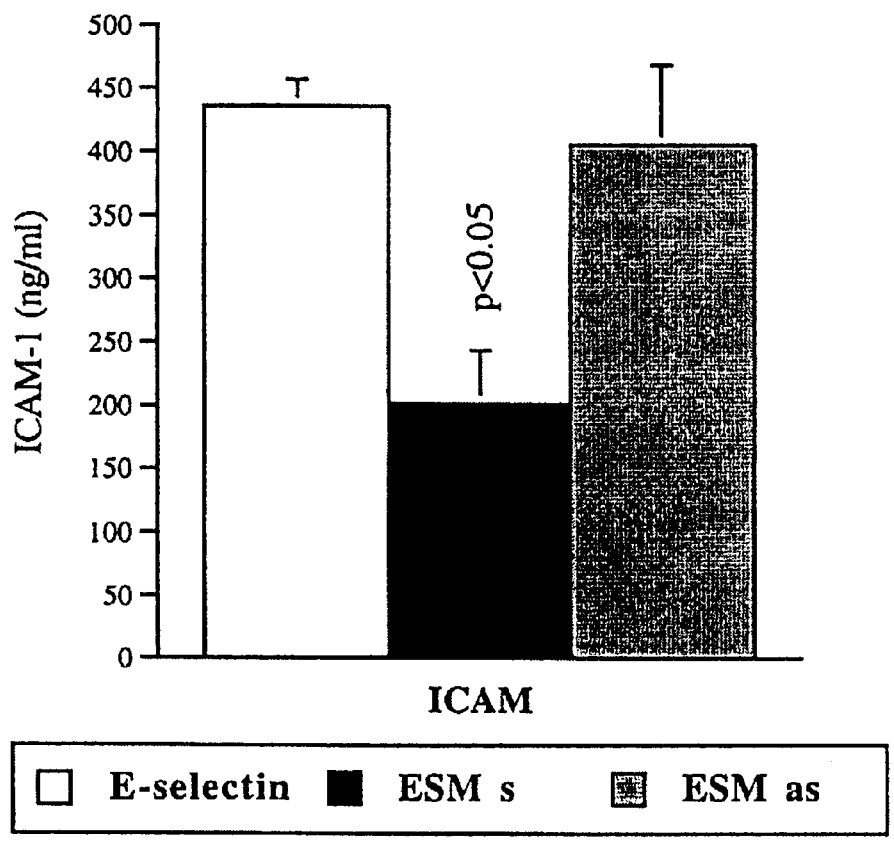

FIG. 11 illustrates the inhibition of ICAM-1 expression in COS cells by ESM-1. ESMs means ESM sense ligated in the pCDM8 vector, ESM as means ESM antisense inversely ligated in the identical vector (pCDM8). ICAM-1 is quantified in ng/ml.

Figure 12:
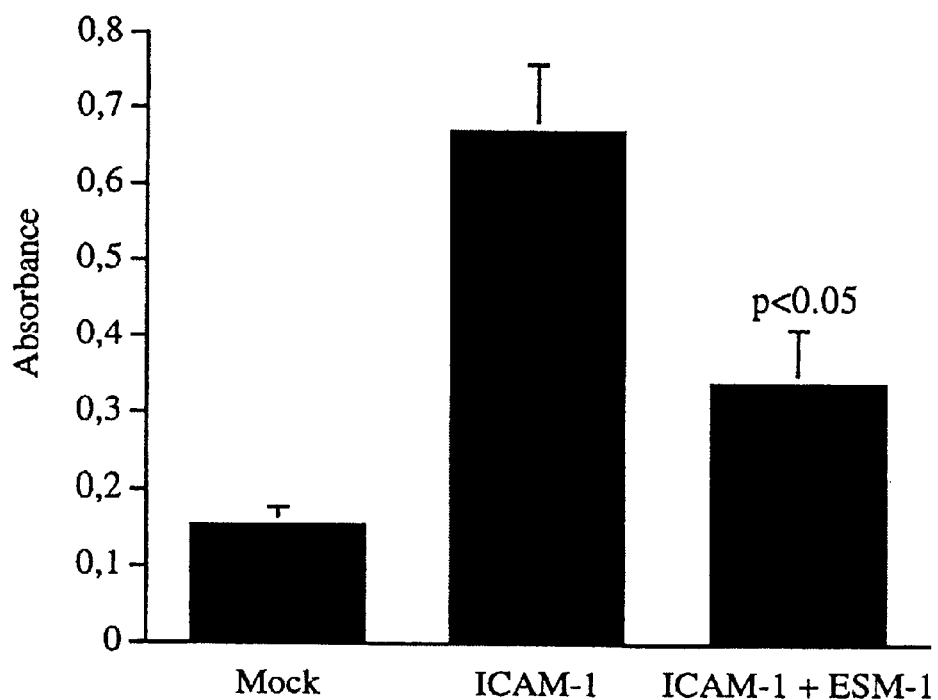

FIG. 12 illustrates the inhibition of ICAM-1 expression at the COS cell surface by a cell ELISA. The expression of ICAM-1 is done in absorbance.

Figure 13A:
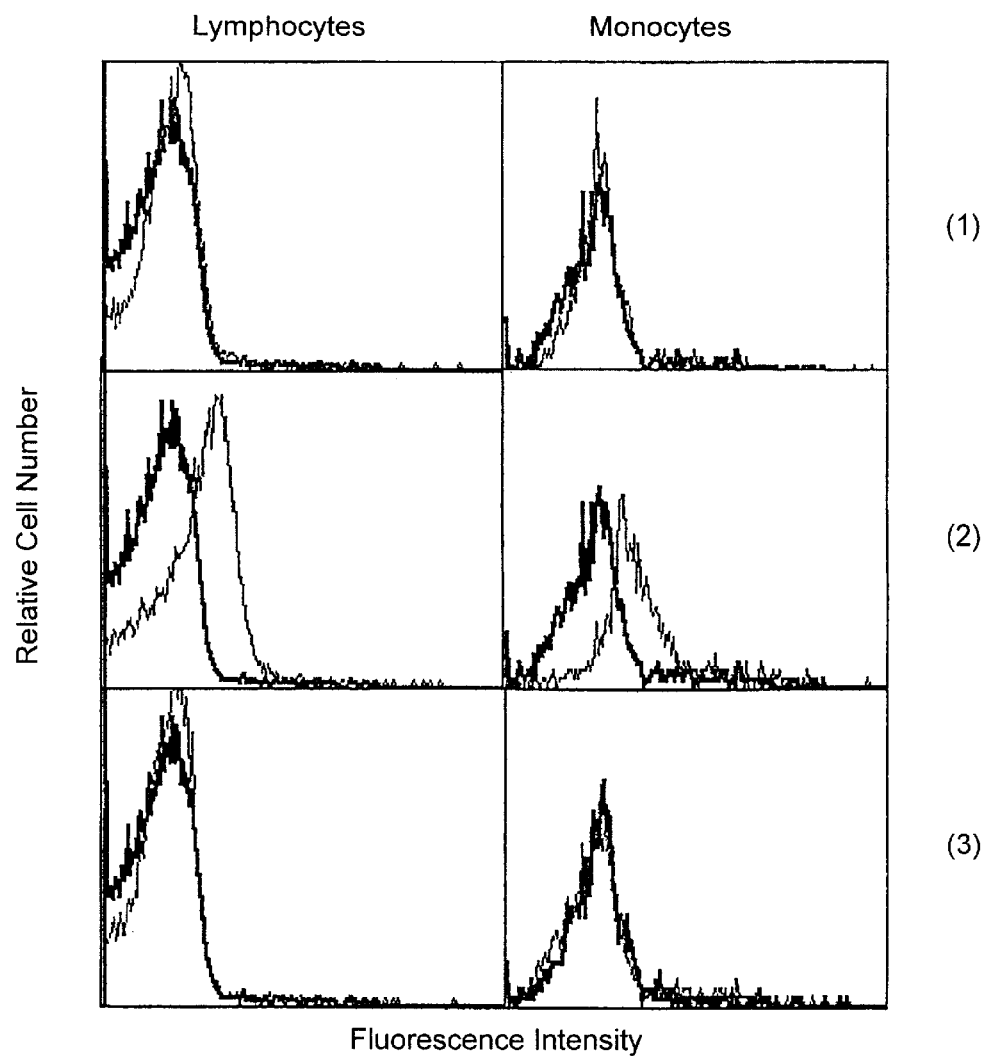
Figure 13B:
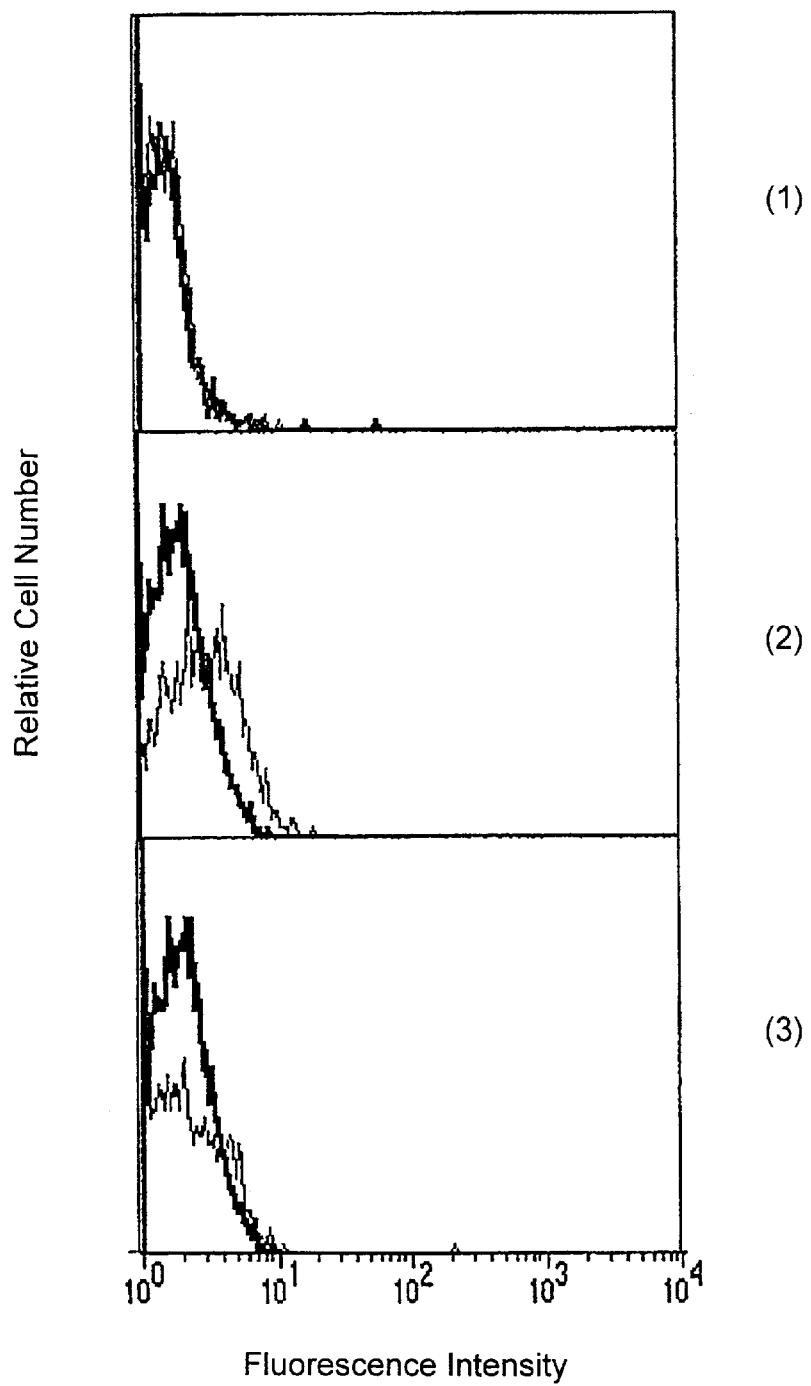

FIGS. 13A–B: ESM-1 binds specifically to the cell-surface of human lymphocytes, monocytes and Jurkat cells. A. PBMC were incubated either in the presence of purified ESM/WT (2), EDTA (5 mM)+ESM/WT (3) or buffer alone (1) for one h at 4° C. Bound ESM-1 was revealed by a specific MEC15 mAb (clear line) versus an isotype-matched IgGl as negative control (bold line), following by a FITC-conjugated anti-mouse IgG and was analyzed by flow cytometry. Lymphocytes and monocytes bound consistently and specifically the wild-type form of ESM-1 (ESM/WT) and this binding activity disappeared in the presence of EDTA. This experiment is representative of three independent experiments. B. Jurkat cells were incubated either in the presence of purified ESM/WT (2), EDTA (5 mM)+ESM/WT (3) or buffer alone (1) for one h at 4° C. Bound ESM-1 was revealed by a specific MEC15 mAb versus an isotype-matched IgGl as negative control, following by a FITC-conjugated anti-mouse IgG and was analyzed by flow cytometry. As observed for PBMC, ESM-1 bound consistently to Jurkat cells, in a divalent-ion dependent manner. This experiment is representative of three independent experiments.

Figure 14:
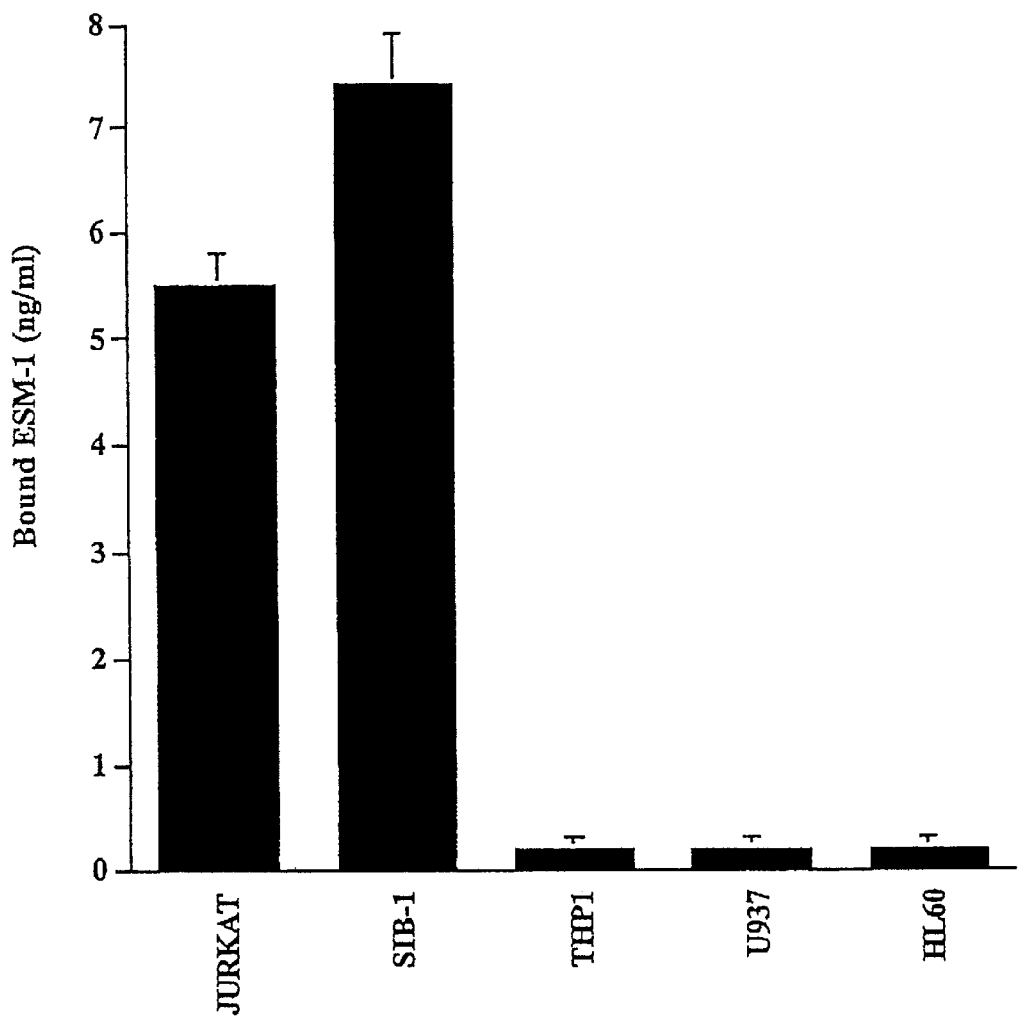

FIG. 14: Analysis of the binding of ESM-1 to different leukocytic cell lines. ESM-1 specifically binds to the lymphoblastoid cell lines. Binding studies of ESM-1 were preformed on lymphoblastoid cell lines (Jurkat and SIB-1), monocytoid cell lines (THP1 and U937) and myeloid cell line (HL60) in a resting state. Cells were incubated in the presence of ESM/WT for one h at 4° C. and detection of bound ESM-1 was quantified in cell lysates by a specific ELISA (n=5).

FIGS. 15A–B: Effects of temperature and PMA activation on ESM-1 binding to Jurkat cells. A. Decrease binding of ESM-1 at 37° C. Ten to 20×10$^6$ jurkat cells were incubated with ESM-1 either at 4° C. or 37° C. for one hour and then washed 3 times with RPMI-1640 buffer at the respective temperatures. Results are expressed as mean±SD of 3 experiments. B. Transient increase of bound ESM-1 upon PMA activation. Ten millions Jurkat cells were incubated at 37° C. for various times with PMA (100 ng/ml) or with medium alone. The cells were quickly cooled on ice and subjected to the ESM-1 binding assay at 4° C. Results are expressed as mean±SD of 3 experiments.

Figure 16A:
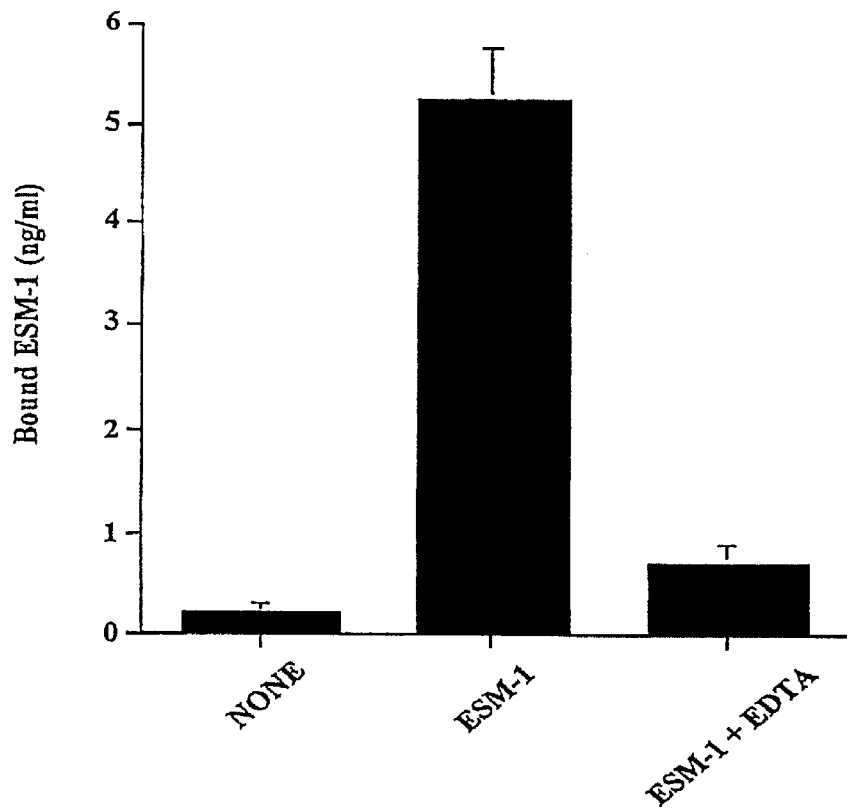
Figure 16B:
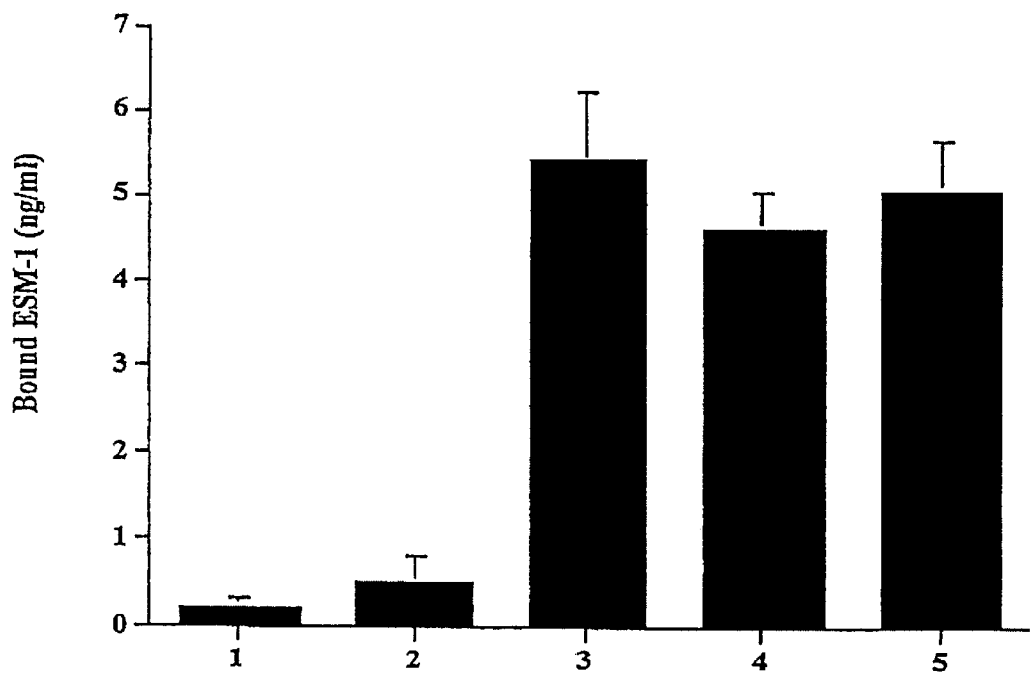
Figure 16C:
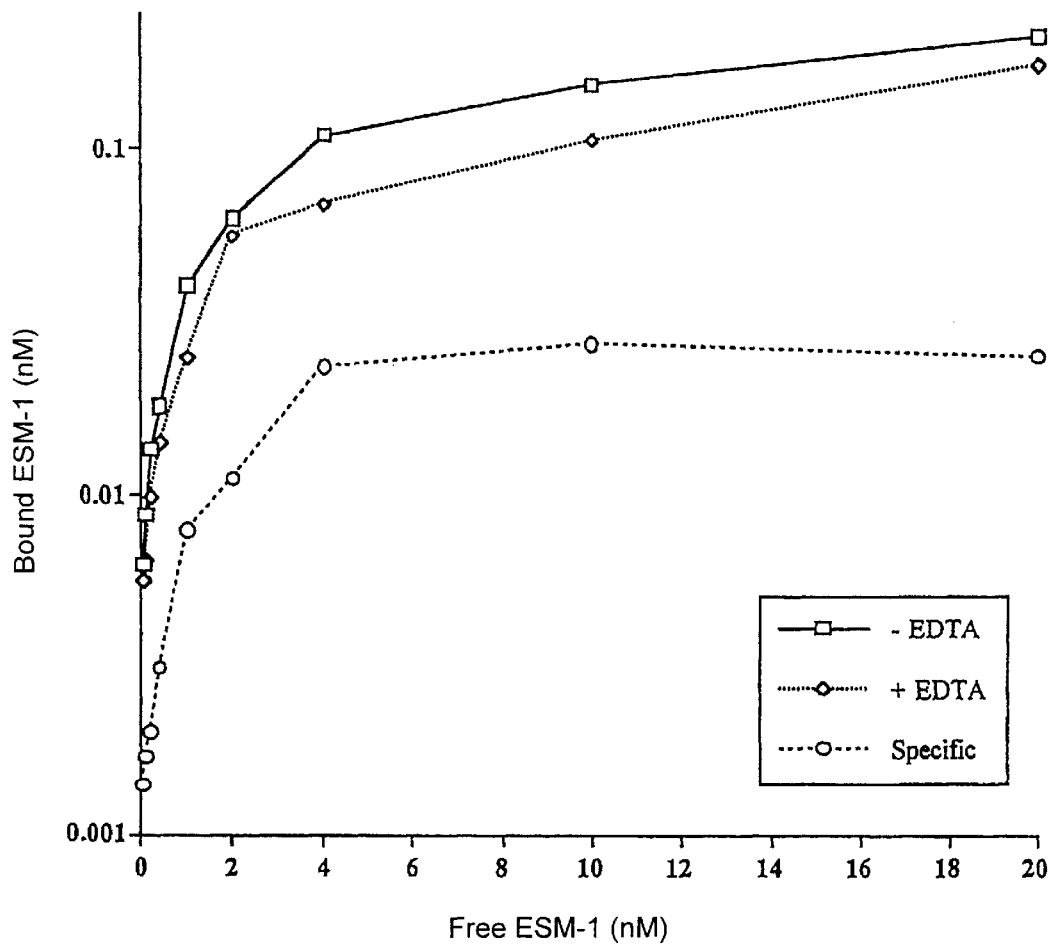

FIGS. 16A–C: Characterization of the divalent ion-dependent and saturable binding to the membrane. A. Abolition of the binding of ESM-1 in the presence of EDTA. Jurkat cells were incubated with ESM-1 or not in the presence of EDTA (5 mM) or not. Cells were washed and lysed. Bound ESM-1 was evaluated by a specific ELISA in lysates (n=5). B. Divalent ions restored the binding activity of ESM-1 to Jurkat cells. As EDTA abolished the binding, binding studies were done in PBS alone (1) or with ESM-1, supplemented with different divalent ions: $Mg^{2+}$ (3), $Mn^{2+}$ (4), $Ca^{2+}$ (5) or none (2). Cells were washed and lysed. Bound ESM-1 was evaluated by a specific ELISA in lysates (n=5). C. The cell-surface binding of ESM-1 to Jurkat cells was saturable. Ten millions of Jurkat cells were incubated with increasing concentrations of ESM-1 in the presence or the absence of EDTA for 1 h at 4° C., then washed and lysed. Bound ESM-1 was detected by specific ELISA in lysates. The bound ESM-1 in the presence of EDTA was substracted to that in the absence of EDTA. The resulting curve represents the divalent ion-dependent bound ESM-1. This curve reached a plateau for an ESM-1 free concentration of 4 nM. These experiment is representative of three distinct experiments.

Figure 17A:
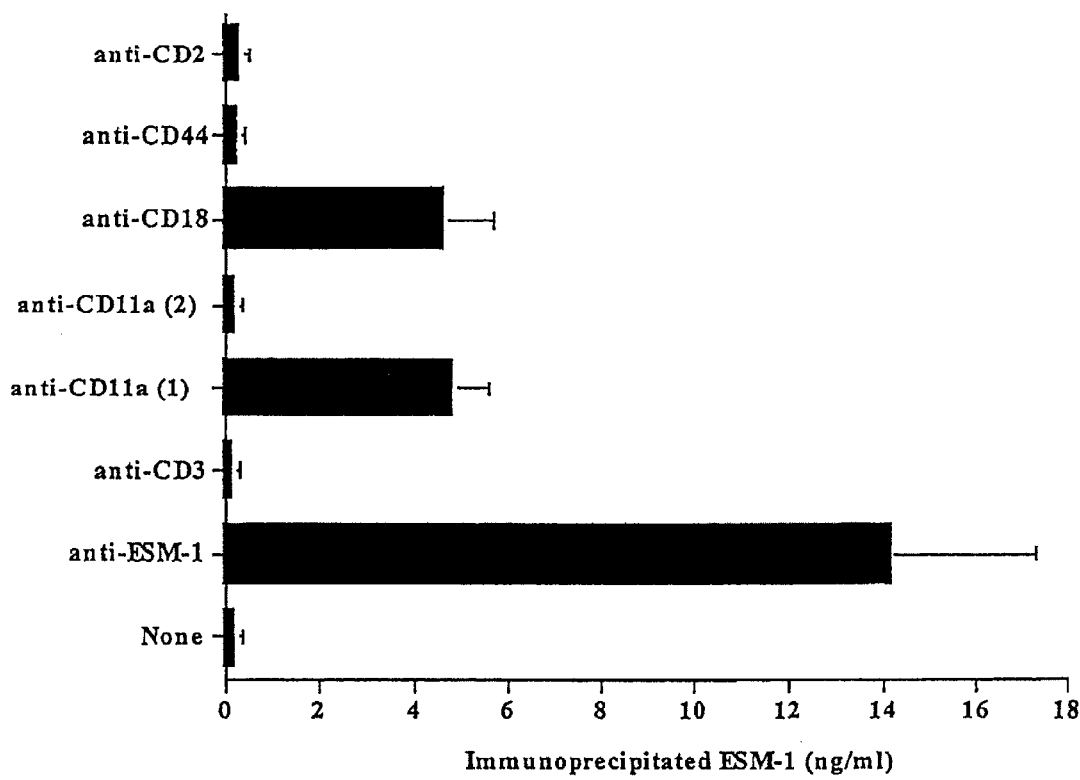
Figure 17B:
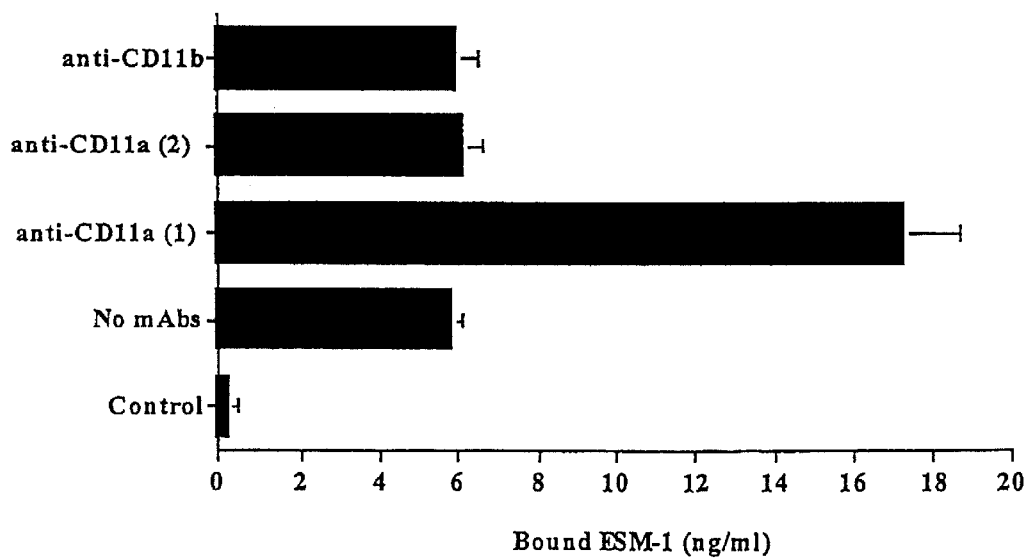

FIGS. 17A–B: An anti-CD11a mAb coimmunoprecipitates ESM-1 with LFA-1 and increases ESM-1 binding to Jurkat cells. A. Coimmunoprecipitation of ESM-1 with LFA-1 : Jurkat cells were incubated with ESM-1 for 1 hour at 4° C. and immunoprecipitations were done with different mAbs according to the procedure previously described (none, anti-ESM-1 (MEC15), anti-CD3, anti-CD11a (1), ie clone HI111, anti-CD11a (2), ie clone G43-25B anti-CD18, anti-CD44, anti-CD2). Beads were washed and eluted. ESM-1 contents from eluates were analyzed by a specific ELISA. B. Activation of the binding of ESM-1 by an anti-CD11a mAb: Jurkat cells were firstly incubated in binding medium with different mAbs (none, anti-CD11a (1), anti-CD11a (2), IgG control) for 1 h at room temperature and secondly with ESM-1 for 1 h at 4° C. Cells were washed and lysed. ESM-1 was quantified by a specific ELISA in lysates (n=5).

Figure 18A:
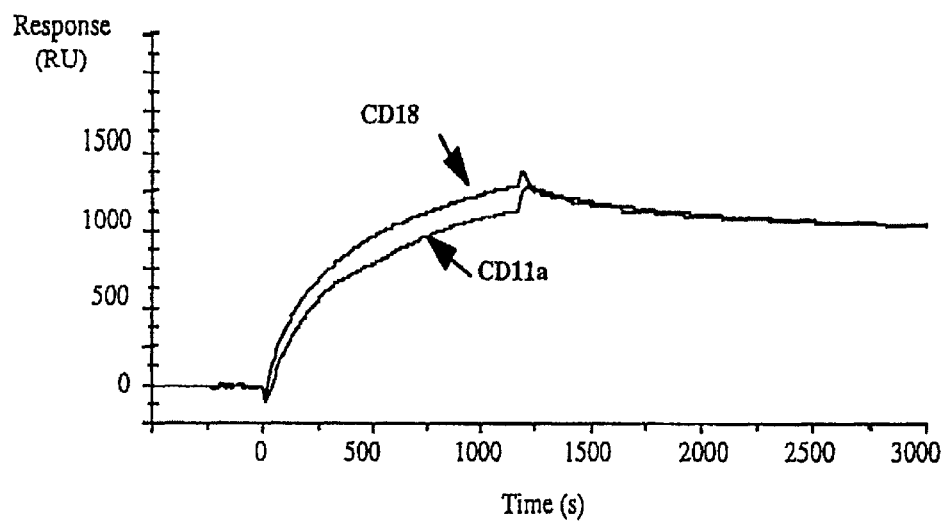
Figure 18B:
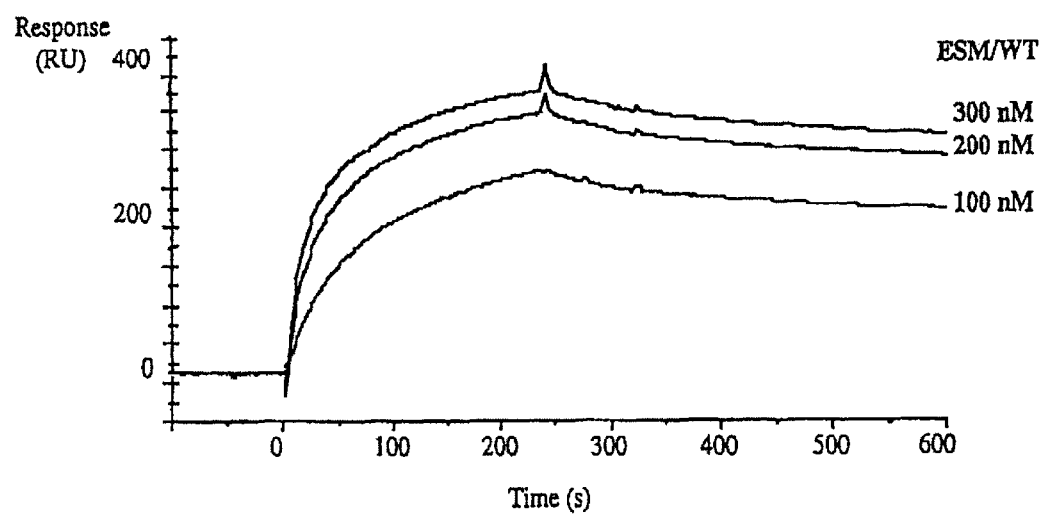

FIGS. 18A–B: A real-time observation of ESM-1-LFA-1 interaction. A. Overlay sensor-grams from the BIAcore analysis demonstrating the capture of LFA-1 on the chip under its heterodimeric form. The heterodimeric CD11a/CD18 molecules were filled on the sensor chip by interacting with a covalently-bound anti-CD11a mAb (HI111) in a first time. Secondly, the capture of both CD11a and CD18 chains was checked by injection of another anti-CD11a mAb (G43-25B) or an anti-CD18 mAb as analyte. Arrows indicate the detection of the CD11a and the CD18 chains. Data are representative of 3 separate experiments. B. Overlay sensor-grams showing the binding of purified human ESM-1 to LFA-1 by BIAcore analysis. Purified ESM-1 was injected in the LFA-1 precaptured channel at the following concentrations: 100, 200 and 300 nM during 250 seconds. Next, the analyte was replaced by running buffer as described in Material and Methods. Association and dissociation rate constants were fitted by using the BIAevaluation software 3.1 allowing to determine the equilibrium affinity constant.

Figure 19:
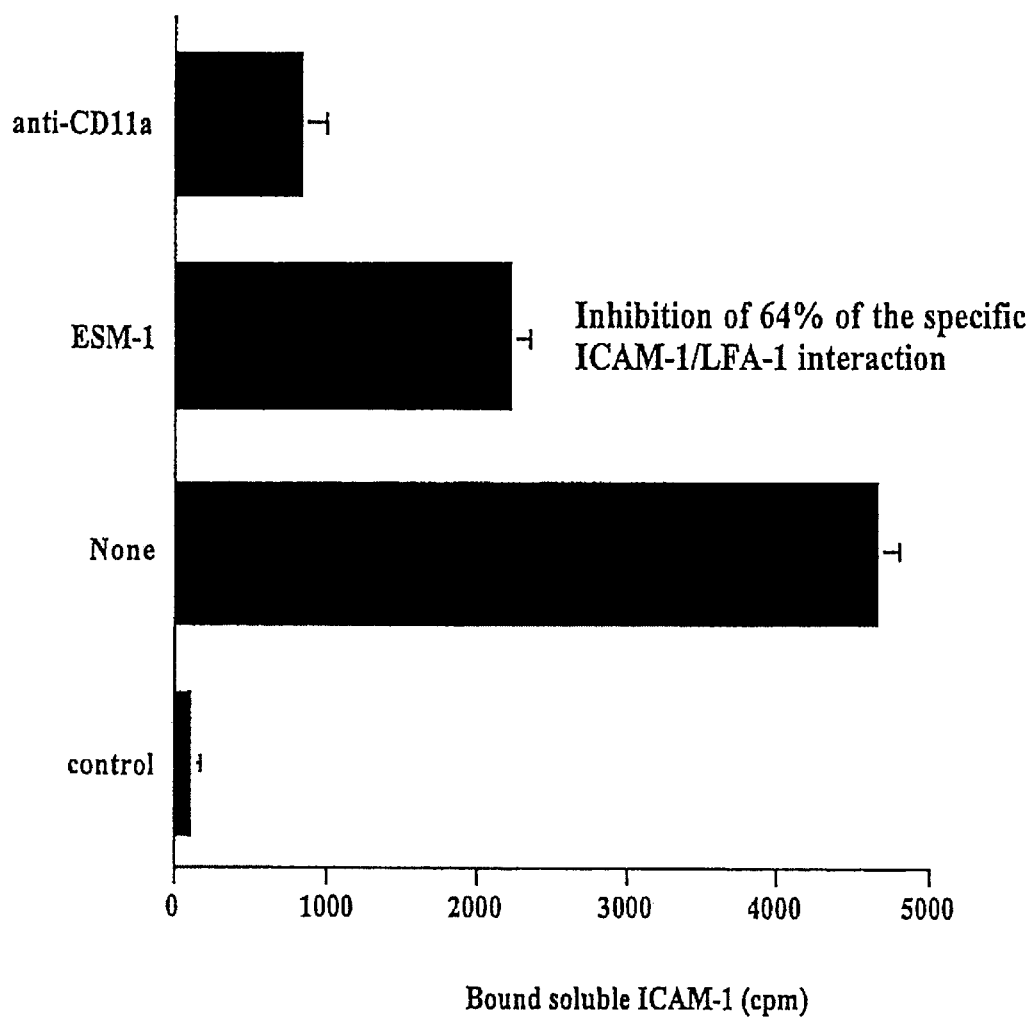

FIG. 19: A. ESM-1 inhibits soluble ICAM-1 binding to Jurkat cells. The Jurkat cells were incubated with or without ESM-1 at 300 ng/mL, or blocking CD11a mAb at 1 microg/mL in the presence of labeled soluble ICAM-1, or not (control) for 1 h at 4° C. Cells were washed and the binding of soluble ICAM-1 was analyzed by cpm counting. Anti-CD11a (clone HI111) strongly blocked the specific binding of soluble ICAM-1 to LFA-1 on Jurkat cells. ESM-1 was able to reduce of 64% the specific binding of soluble ICAM-1 (n=5). B.

Dose-response inhibition of ICAM-1 binding by ESM-1. Results are expressed as a mean of percentage of inhibition from 2 to 3 experimental data for each point.

Figure 20:
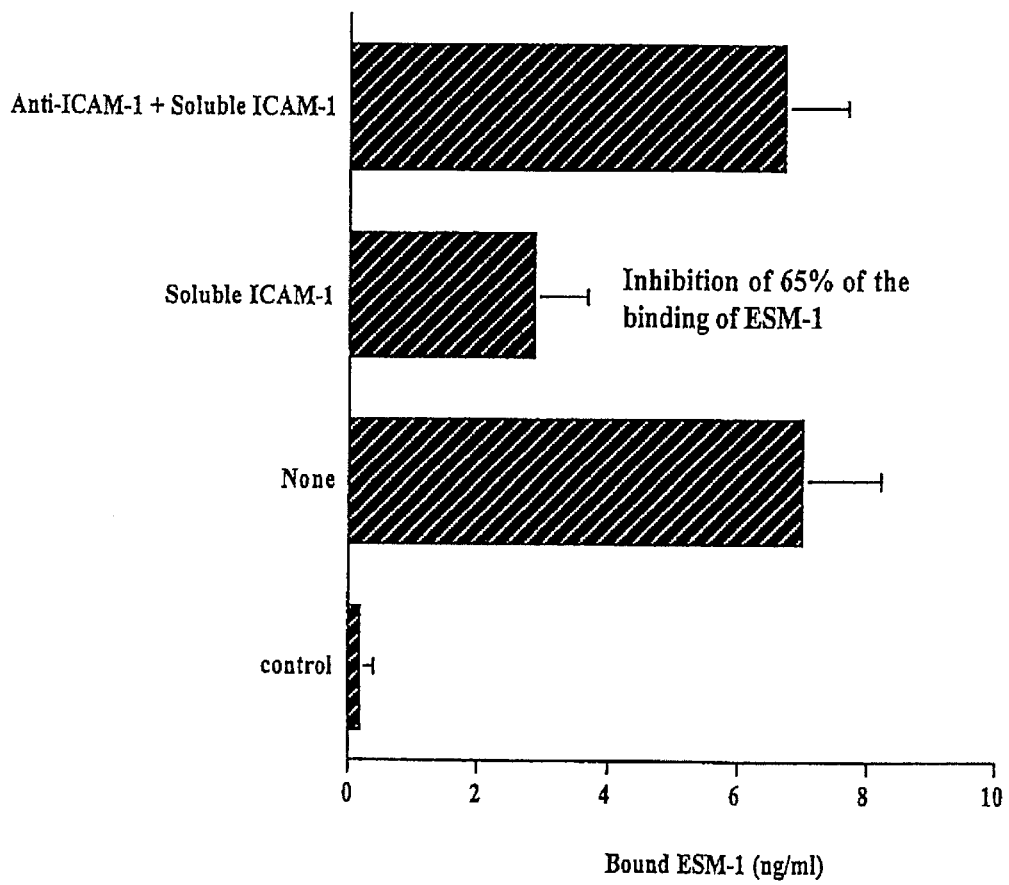

FIG. 20: Soluble ICAM-1 inhibits ESM-1 binding to Jurkat cells. Jurkat cells were incubated with or without soluble ICAM-1 at 300 ng/mL, or soluble ICAM-1 supplemented with blocking ICAM-1 mAbs at 1 microg/mL, in the presence of ESM-1 at 300 ng/mL or not (control). ESM-1 binding was evaluated by a specific ELISA. Soluble ICAM-1 inhibited of 65% the binding of ESM-1 to Jurkat cells and this inhibitory effect could be specifically abolished by co-incubation with blocking anti-ICAM-1 mAbs (n=5).

Figure 21:
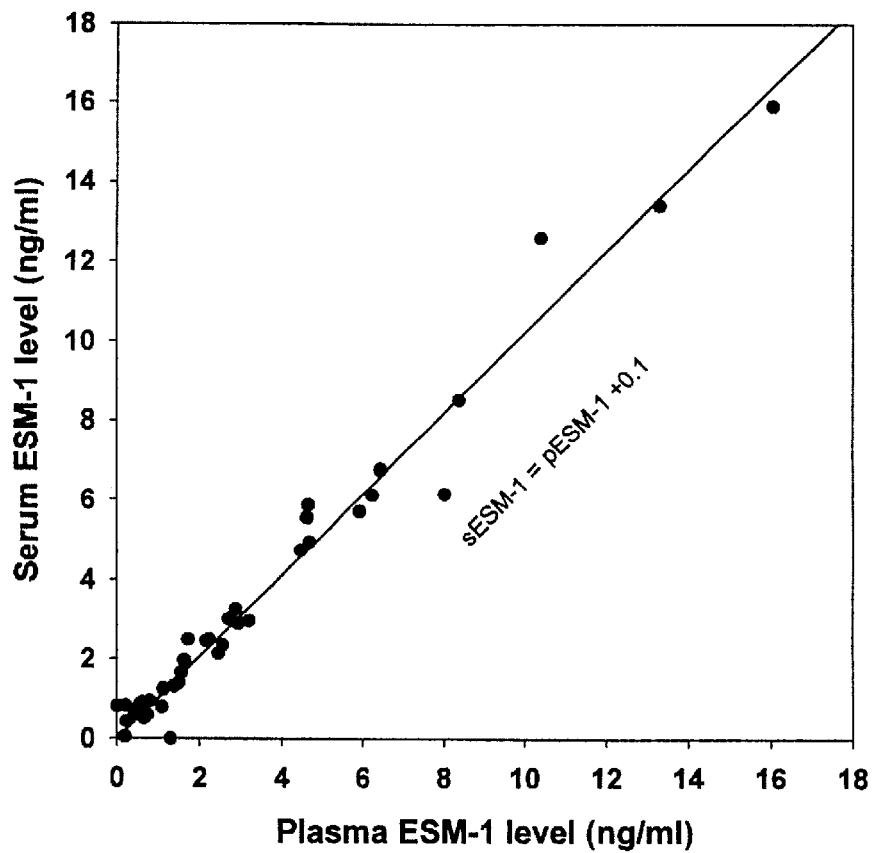

FIG. 21: Comparison of serum and plasma levels of ESM-1 in healthy subjects and in patients. Serum ESM-1 level expressed as ng/ml is depicted in ordinates and Plasma ESM-1 level expressed as ng/ml is depicted in abscissa.

Figure 22:
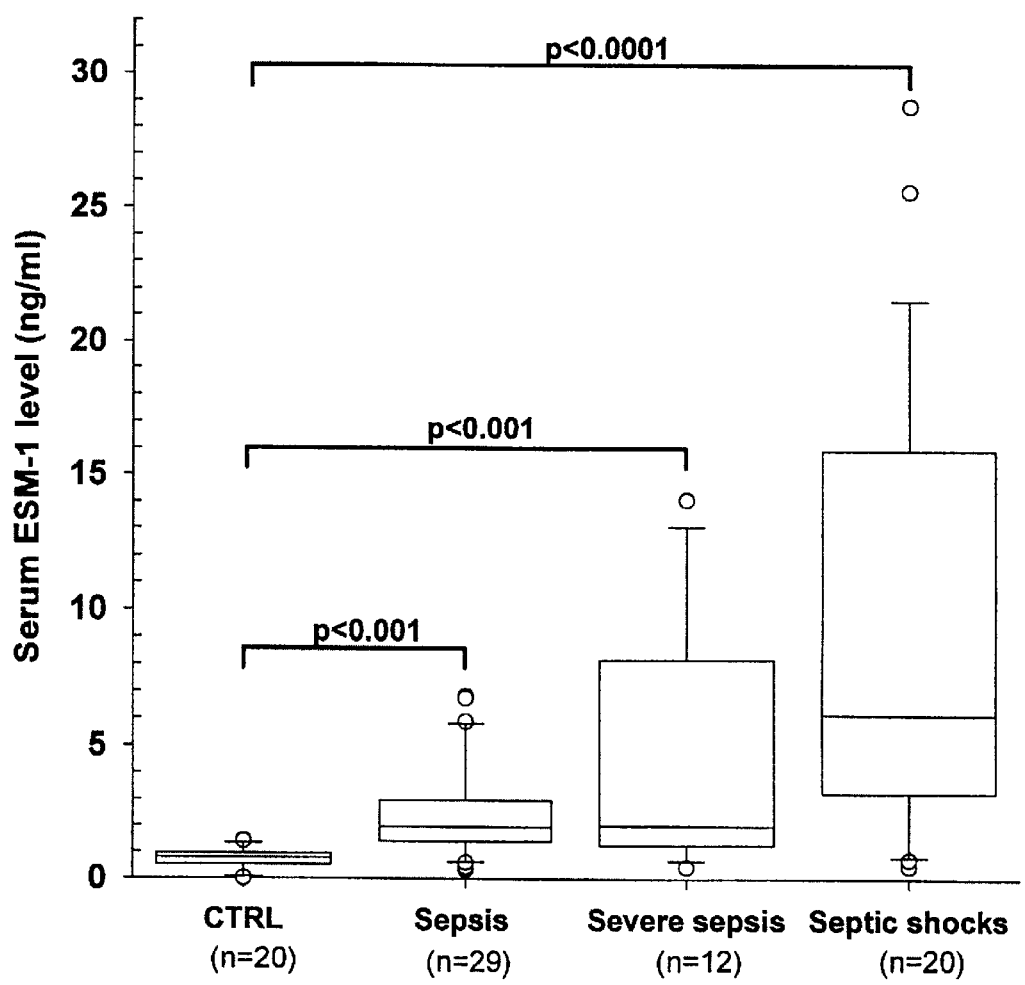

FIG. 22: Serum ESM-1 level in control and patients groups. Serum ESM-1 level expressed as ng/ml is depicted in ordinates. Healthy volunteers (CTRL) and three groups of patients are depicted in abscissa. The p value between the control group and each of patients group is indicated on the Figure.

Figure 23:
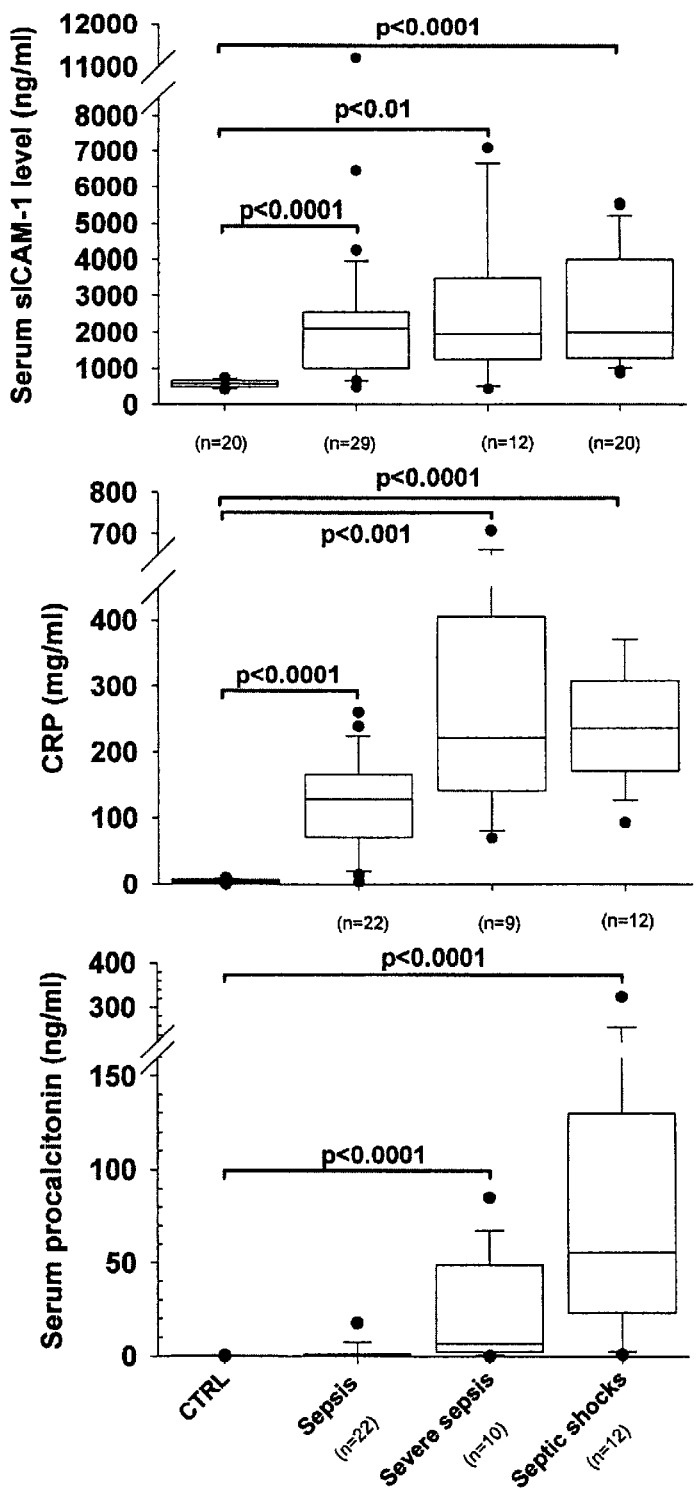

FIG. 23: Serum soluble ICAM-1, C-Reactive Protein and procalcitonin in control and patients groups. Serum levels of soluble ICAM-1 (FIG. 23A), C-Reactive Protein (FIG. 23B) and Procalcitonin (FIG. 23C) is depicted in ordinates and expressed as ng/ml. Healthy volunteers (CTRL) and three groups of patients are depicted in abscissa. The p value between the control group and each of patients group is indicated on the Figure.

Figure 24:
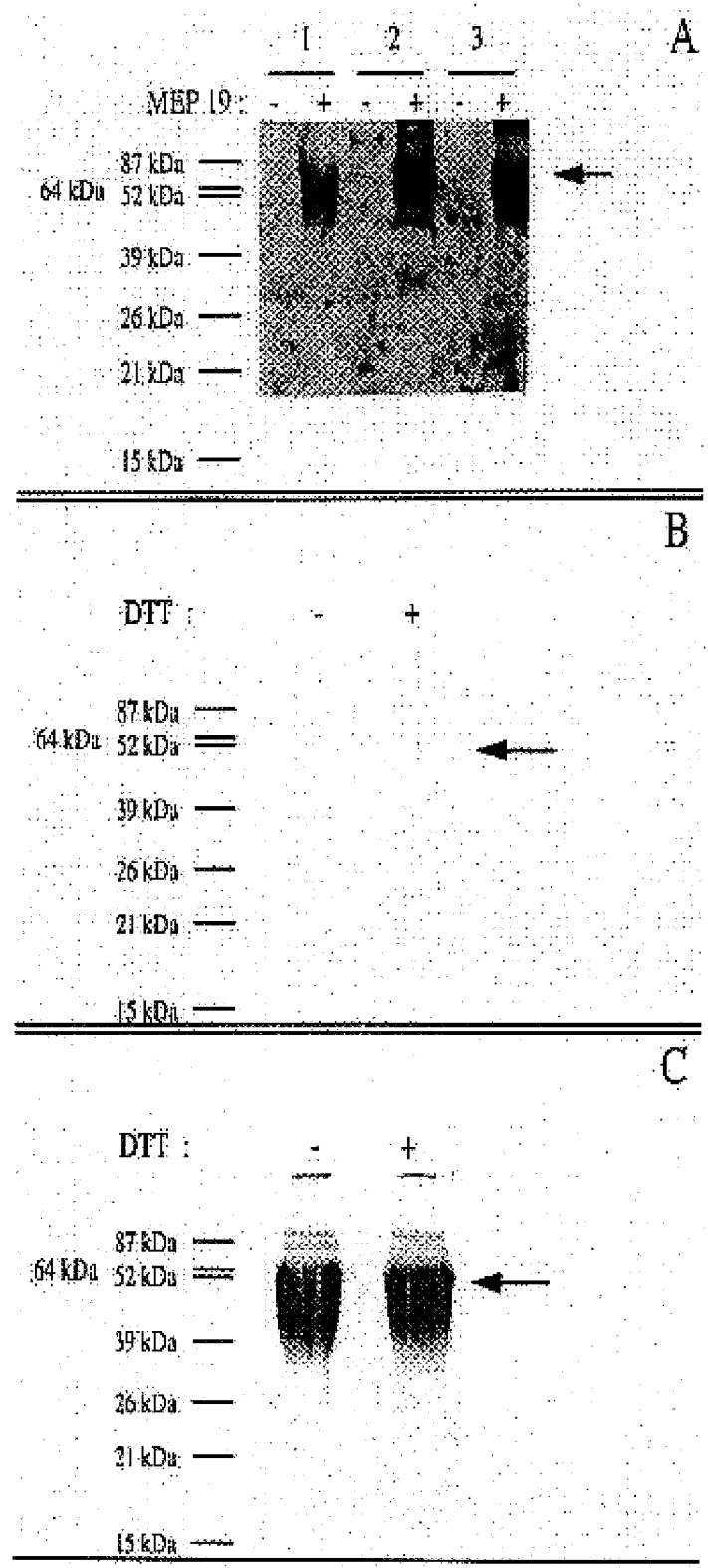

FIGS. 24A–C: Western-blots and dye staining of ESM-1 on SDS-PAGE. Each immunoblot was probed with MEP 14 anti-ESM-1 mAb at 1 mg/ml. The second HRP-labeled anti-mouse antibody was affinity-purified and yielded negative results when used alone. A. Immunoblots of ESM-1 from different cell types expressing ESM-1 from different cell types expressing ESM-1. Immunoprecipitations of ESM-1 from SV1 (1), 293-ESM(2° AND CHO-ESM(3)

supernatants were performed with MEP 19 when indicated or with control antibody.

Arrow indicates the specific band. Secreted form of ESM-1 is represented by a diffuse band around 50 kD. A. Absence of detection of purified ESM-1 with Coomassie blue, 5 mg of purified ESM-1 from SV1 cells was loaded on 15% SDS-PAGE and was checked by coomassie blue staining in order to detect the peptidic core of the molecule. Arrow indicates the absence of detection of ESM-1. C. Detection of purified ESM-1 with alcian blue. 5 mg of purified ESM-1 from SV1 cells was loaded on 15% SDS-PAGE and was revealed by alcian blue staining in order to detect the glycanic core of the molecule. Arrows indicates ESM-1.

EXAMPLES

The following examples illustrate selected aspects of the invention but are not intended to limit it.

Materials and Methods of Examples 1 to 5

Cell culture. Human endothelial cells were derived from umbilical vein (HUVEC) by collagenase treatment and cultured in RPM1 1640 supplemented with 20% fetal calf serum, 2 mM L-glutamine, 10 $\mu$g/ml heparin and 25 $\mu$g/ml endothelial cell growth supplement (Sigma). HUVECs were cultured in 0.5% gelatin-coated six-well culture plates (Falcon). At confluence, HUVECs were washed two times and incubated overnight before cytokine stimulation with RPM1 1640 containing 20% fetal calf serum. Before additon of cytokines, HUVECs were washed once and incubated in RPMl1640 containing 5% fetal calf serum. Cytokines were then added to cell culture of TNF$\alpha$)200 units/ml, a gift from Dr. J. Wietzerbin), IFNY (1000 units/ml, Genzyme Corp.), IL-1$\beta$ (10 units/ml, Genzyme), IL-4 (1000 units/ml, Roche Research Gent). After cytokine activation, the cells were lysed in 4 M guanidine thiocyanate buffer, and total RNA was isolated as described below. SV40-transfected human endothelial cells (SV1 cells) were cultured in RPMl1640 containing 2 mM L-glutamine and 10% fetal calf serum (LASSALLE et al. (1992) Eur. J. Immunol. 22, 425–431). Dami cells were maintained in Dulbecco's modified Eagle's medium supplemented with 10% horse serum. Hela and COS cells were maintained in Dulbecco's modified Eagle's medium supplemented with 10% horse serum; fetal calf serum; MO7 cells were maintained in Iscove's modified Dubelcco's medium supplemented with 10% fetal calf serum; and HL60, Jurkat, Daudi and TF1 cells were maintained in RMPl1640 supplemented with 10% fetal calf serum.

Construction of cDNA Libraries—Poly(A) RNA was isolated from SV1 cells using the FastTrack mRNA isolation kit-(Invitrogen) Poly (A) RNA was primed with an oligo (dT)-Xhol primer adaptor (Stratagene, Inc.) cDNA was synthetized from 3 $\mu$g of poly(A) RNA as recommended by the manufacturer (Stratagene). EcoRl adaptor was added to the cDNA by blunt-end ligation following by exposure to Xhol restriction endonuclease. cDNA was fractionated by agarose gel electrophoresis and cDNA longer than 500 bp was ligated into the predigested EcoRl-Xhol sites of $\lambda$ Zap II vector (Stratagene). A second CDNA library was also constructed. Poly(A) RNA was primed with an oligo(dT)-Notl primer adaptor (Promega). The buffers and enzymes used for cDNA synthesis were purchased from Life Technologies, Inc. BstXl adaptor was ligated to the cDNA blunt ends, and the cDNA was fractionated by agarose gel electrophoresis. The cDNA between 1 and 3 kb was ligated into BstXl cut pCDM8 vector. The construct was transfected into *Escherichia coli* MC1061 P3 by electroporation (Bio-Rad Gene Pulser). The libraries consisted of $1.7 \times 10^7$ plaque forming units/$\mu$g and $10^5$ independent colonies, respectively, with an average size of 2 kb.

Cloning and Sequence Analysis. The initial 1.2-kb fragment of ESM-1 was cloned by immunoscreening of $5 \times 10^5$ recombinant phages with a rabbit immune serum raised against an immunoprecipitate of supernatant from $4 \times 10^9$ human blood platelets (LASSALLE et al. (1993) Eur. J. Immunol. 23, 796–803). Immunoscreening was performed as described (Sambrook, E. et al. (1989) Molecular Cloning; A Laboratory Manual, Cold Spring Harbor Laboratory, N.Y.). Anti-E coli antibodies were removed from serum by adsorption against nitrocellulose filters pre-soaked with *E. coli* lysates. The nitrocellulose filters were incubated in a quenching buffer (5% non fat milk in PBS) for 30 minutes, followed by an overnight incubation at 4° C. with constant agitation in 1:200 diluted rabbit antiserum. After washing four times with PBS, bound antibody was detected by a 2-h incubation with peroxidase conjugated goat antirabbit IgG (Tago Immunoloigcals, Burlingame, Calif.). The nitrocellulose filters were then rewashed and developed with HRP color development reagent (Bio-Rad). Three distinct cDNA clones were further isolated by two rounds of purification. The recombinant pBluescript plasmids were excised in vivo from the lambda phage as recommended by the manufacturer (Stratagene, La Jolla, Calif.). These cDNAs were subsequently sequenced (T7 Sequencing Kit, Pharmacia Biotech, Inc.) and used as probes in Northern Blot analysis. The full length CDNA from ESM-1 was recloned as following: a total of 10,000 independent colonies from a HUVEC CDNA library construced in pCDM8 vector were lifted on nylon membranes (Hybond membranes, Amersham Corp.). Cell lysis, neutralization, washing, and UV cross-linking were performed as described (E. Sambrook et al. (1989) Molecular Cloning: A Laboratory Manual, Cold Spring Harbor Laboratory, Cold Spring Harbor, N.Y.). High stringency hybridization was performed at 65° C. in 6×SSC, 5×Denhardt's solution, 0.5% SDS, 40 $\mu$g/ml denatured salmon sperm DNA, and 0.25 mM EDTA. The filters were washed two times for 30 min. at room temperature with 2×SSC, 0.1% SDS and two times for 30 min. at 65° C. with 0.1×SSC, 0.1% SDS. Positive colonies were picked and purified. A cDNA of 2 kb was isolated and subsequently subjected to sequencing on both strands. Sequence analysis was performed using PCGENE (IntelliGenetics), WORD-SEARCH, and FASTA (UWGCG) programs with GenBank™, EMBL, and SwissProt data bases.

Northern and Southern Blot Analysis and Probe Labeling. Total RNA from various cells and from HUVECs was isolated by phenol and chloroform extraction followed by precipitation with isopropanyl alcohol. Ten to thirty micrograms total RNA per lane were electrophoresed through 1% formaldehyde agarose gels and transferred to a nylon membrane (GeneScreen, DuPont NEN). Five micrograms of 0.24–9.5 kb RNA ladder (Life Technologies, Inc.) were used for RNA sizing. High stringency hybridization was performed at 42° C. in 1 M NaCl, 50% formamide, 1×Denhardt's solution, 10% dextran sulfate and 100 $\mu$ml denatured salmon sperm DNA. The membranes were washed two times for 30 min at room temperature with 2×SSC, 0.1% SDS, and two times for 30 min at 55° C. with 0.1×SSC, 0.1% SDS. Southern Blot was hybridized at 65° C. in 6×SSC, 5×Denhardt's solution, 0.5% SDS, 40 $\mu$g/ml denatured salmon sperm DNA, and 0.25 mM EDTA. The washing step consisted of two times for 30 min at room temperature with 2×SSC, 0.1% SDS and two times for 30 min at 65° C. with 2×SSC, 0.1% SDS. Hybridized membranes were exposed to x-ray film at −70° C. overnight for 2 weeks. The ESM-1 cDNA probes were either the 1.2-kb EcoRl-XhoI initial fragment (3' end), or the 1176-bp Hindlll fragment from the 5' end of the ESM-1 CDNA. The other DNA probes were: E-selection probe (PstI-EcoRl fragment, British Biotechnology), lCAM-1 probe (EcoRl-XhoI fragment, British Biotechnology), vascular cell adhesion molecule-1 (EcoRl-XhoI fragment, a RT-PCR construction from TNF-activated HUVECs cloned in pcDNA3 (Invitrogen) and human β-actin (Clontech IS Laboratories, Inc.). All of these probes were labeled by random priming (Multiprime DNA labeling system, Amersham Corp.).

Reverse Transcription -PCR was performed with RNA from each of the cell sample shown in multiple cell Northern Blot. Five micrograms of total RNA were reverse transcribed with a $dT_{12-18}$ oligonucleotide primer as recommended by the manufacturer (reverse transcriptase Rnase H-minus. Life Technologies, Inc.). The specific primers used were ESM-1 forward primer showing SEQ ID No. 4 (5'GTTCTTTGACTTTGATGT3') and ESM-1 reverse primer showing SEQ ID No. 5 (5'CAACTCTGTTGGCCAAACT3'); these primers yield a specific DNA fragment of. 1042 bp. The human glyceraldehyde-3-phosphate dehydrogenase primers were purchased from Clontech. PCR amplification was performed for 30 cycles with a "hot start" at 92° C. for 2 min following by 94° C. denaturation for 30 s, 51° C. hybridization for 1 min, and 72° C. extension for 1 min 30 s. RT-PCR products were resolved in a 1% agarose gel in 1×TAE buffer.

In vitro Translation Assay. The 5' Hindlll-Xbal fragment of ESM-1 (686 bp) was cloned into pcDNA3 vector. In vitro coupled transcription/translation assay was performed using T7 RNA polymerase coupled with a rabbit reticulocyte lysate as described by manufacturer (Promega). One microgram of DNA was added in 25 µl of final reaction buffer containing [$^{35}$S] methionine. The cotranslational and initial post-translational processing of ESM-1 protein was studied by addition of microsomal vesicles, which were added at various concentrations (Promega). The translation products were analyzed by SDS-PAGE.

Fusion Protein Constructions and Expression. The XmaI-digested fragment of ESM-1 was fused in frame to glutathione S-transferase open reading frame and was expressed in E. coli with the use of a pGEX-2TK vector (Pharmacia). Synthesis of the fusion protein was induced by addition of 0.5 mM isopropyl-1-thio-β-D-galactopyranoside (Boehringer Mannheim) for 4 h at 37° C. The cells were centrifuged and resuspended in PBS containing 1% Triton X-100 and a mixture of protease inhibitors (Life Technologies, Inc.). The fusion protein was purified on glutathione-Sepharose 4B column as recommended by the manufacturer (Pharmacia). After the washing step, the Sepharose beads were resuspended in 20 ml of PBS containing 10IU of thrombin (Sigma) and incubated 2 h at room temperature. After centrifugation, the supernatants were concentrated by centrifugation on a Centricon 10 filter (Amicon), and the protein content was evaluated with a standard protein assay (Bio-Rad). One liter of bacterial culture yielded approximately 40 µg of purified ESM-1 protein.

Preparation of Polyclonal Immune Serum. Fifty micrograms of purified ESM-1 protein were mixed with complete Freund's adjuvant and injected in a New Zealand White rabbit. Boost immunizations of 40 µg were given at 4 Week intervals in incomplete Freund adjuvant. The rabbit was bled 4 weeks after the first boost immunization. Immune serum was analyzed first by immunoblotting of Sf9 cell supernatants infected with ESM-1 recombinant baculovirus. The Sf9 cells infected or not infected with the hIL-5 recombinant baculovirus (Guisez et al. (1993) FEBS Lett. 331, 49–52) served as control supernatants.

Metabolic Radiolabeling and Immunoprecipitation. The expression construct pcDNA3-ESM-1 was generated by subcloning the Hindlll-Xbal insert of ESM-1 into the Hindlll-Xbal digested pcDNA3 vector. This construct was transfected into COS cells using the DEAE-dextran method. After 48 h, cells were replated into 25-cm$^2$ culture flasks, and 24 h later, both ESM-1 and mock tranfectants were metabolically labeled with [$^{35}$S]methionine (100 µCi/ml) for 6 h. COS cell supernatants were collected by centrifugation, and COS cells attached to the plates were washed twice with PBS before cell lysis with PBS containing 0.5% Nonidet P-40 and a mixture of protease inhibitors. Five hundred microliters of PBS containing protease inhibitors were added to 500 µl COS cell supernatants and COS cell lysates. These preparations were incubated with 5 µl of rabbit immune serum and incubated overnight at 4° C. with constant agitation. Protein A-Sepharose CL-4B was added to the mixtures, which were then incubated for 90 min at room temperature. The beads were then washed by centrifugation twice with PBS, 0.5% Nonidet P-40 and twice with PBS. Twenty microliters of SDS-PAGE sample buffer were added to the beads, which were then heated at 100° C. for 2 min. After centrifugation, the supernatants were run on a 15% SDS-polyacrylamide gel. The gels were dried and exposed to x-ray film at −70° C.

In Situ Hybridization—Cryostat sections were fixed in 4% paraformaldehyde in PBS, dehydrated through graded alcohols, and stored at 4° C. A Hindlll-BamHl ESM-1 CDNA fragment (0.3 kb from the 5' region of ESM-1) was subcloned into a pBluescript vector and linearized with Hindlll or BamHl to produce antisense or sense probes. Transcription was performed in the presence of $^{35}$S-cytidine triphosphate and the appropriate T3 or T7 RNA polymerases for antisense and sense riboprobes. Hybridization and autoradiography were kindly performed by Dr. A. Tsicopoulos as described previously (Hebbard et al. (1995) Arthritis & Rheum. 38, 406–412).

Example 1 cDNA Cloning and Sequence Analysis of EMS-1

The initial immunoscreening of a HUVEC cDNA library was designated to isolate cDNA encoding a 55 kDa autoantigen putatively involved in severe asthma (Lassalle et al. (1993) Eur. J. Immunol. 23, 796–803). This antigen was enriched by immunoprecipitation from thrombin-activated human blood platelets, which share immunoloigcally the common 55 kDa antigen. A rabbit antiserum was raised against this antigen and used to screen the HUVEC cDNA library. 5×10$^5$ clones were screened with the subsequent isolation of 3 cDNA clones. These cDNA were sequenced, and sequence comparison to GenBank™ and EMBL data bases revealed unique identities for two of these three cDNAs. Multiple human cell Northern Blot analysis using these cDNAs as probes revealed that one hydribized only in HUVECs and SV1 cells but not in the other cell lines tested. These data suggested that this cDNA of 1.2 kb was derived from an RNA messenger that encodes a molecule highly restricted to human endothelial cells. We have called this molecule ESM-1 (Endothelial Cell Specific Molecule 1). Thus, the full length ESM-1 cDNA was cloned in a size-selected HUVEC cDNA library construced in pCDM8, 10,000 independnet colonies were screened, and one clone was purified. This clone had shown an inverted cDNA insert of 2 kb.

Sequence Analysis of ESM-1

Figure 1A:
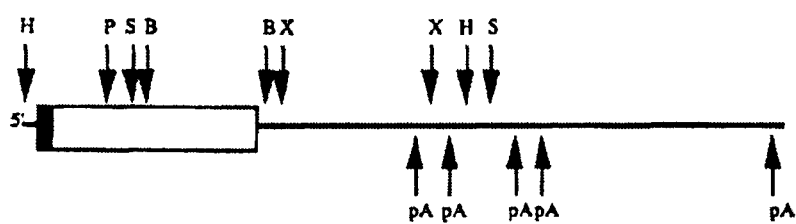
FIG. 1A is a partial restriction map of ESM-1 cDNA. H. Hindlll, P stl; S. Smal; B. BamHl; X, Xbal; pA, polyadenylation site. The putative signal peptide is the dark box. The coding sequence is in white box B.

The complete cDNA sequence, 2006 base pairs in length, contains an open reading frame of 552 nucleotides (FIG. 1). A Kozak consensus sequence for translation initiation was identified at nucleotide 56 (AACATGA) (Kozak M. (1986) Cell 44, 283–292, Kozak M. (1987) Nucleic Acids Res. 15, 8125–8148). The 1398 nucleotide 3'-untranlated region encodes a MRNA with 66% AU nucleotides. It includes several domains involved in MRNA instability; 10 AUUUA domains and 3 UAUUUA(U/A) domains (Shaw G. et al. (1986) Cell 46, 659–667, Lagnado et al. (1994) Mol. Cell. Biol. 14, 7984–7995) The 3'-untranslated region contains five putative polyadenylation consensus sequences (AAUAAA) (Proodfoot et al. (1976) Nature 263, 211–214) at nucleotides 1045, 1132, 1404, 1495, and 1987; the last one is located just 14 bp upstream from the poly(A) sequence. DNA data base searches did not reveal any significant homology with our nucleotide sequence. The cDNA is predicted to code for a protein of 184 amino acids. The predicted $NH_2$-terminal hydrophobic signal sequence (Von Heijne (1986) Nucleic Acids Res. 14, 4683–4690) is composed of 19 amino acids. The mature protein, predicted to contain 165 amino acids, does not contain any potential N-glycosylation site.

To confirm the correct assignment of the open reading frame, we performed an in vitro translation. ESM-1 cDNA was cloned into the Hindlll-Xbal sites of the pcDNA3 vector. SDS-PAGE analysis of the primary in vitro coupled transcription-translation product migrated at an apparent molecular mass of 22 kDa in reducing condition. This primary translation product was shown to be truncated (2 kDa) with the addition of microsomal vesticles, which indicates that the signal sequence is functional. ESM-1 a cysteine-rich protein, containing 18 Cys residues. No known:

protein motifs were found in the ESM-1 protein. Searches with the FASTA program did not result in the identification of protein homology up to 35%. The best protein similarities were found with the human β2 integrin (cysteine-rich tandem repeats; 27.6% identity and 54.6% similarity), the human IGF binding proteins (32% identity and 55.3% similarity), the human fibrillin 1 (28.8% identity and 54.3% similarity, laminin β2 (31.4% identity and 52.6% similarity), and human procollagen α2(24.2% identity and 44.6% similarity (FIG. 2).

Example 2

ESM-1 Gene Expression

Multiple human cell lines were analyzed by Northern Blot.

ESM-1 specific DNA probes hybridized strongly to HUVECs and SV40-transfected HUVECs (FIG. 3A). One major band was seen with an apparent size of 2.2 kb. A weak band was also seen in COS cells, but this band was considered non specific because its size corresponded to the 28S rRNA, and RT-PCR analysis with COS RNA did not reveal any specific band compared to HUVEC RNA (FIG. 3B). No other bands could be detected, whatever probe was used (probes included either the coding sequence or the 3'-UTR). Strikingly, this band was undetectable in any of the cell types other than HUVECs and SV1 cells, even after x-ray exposure up to 2 weeks. Apparent cell-specific expression was also observed with RT-PCR of RNA from each of the cell sample using specific primers from ESM-1 cDNA. A strong signal of 1042 bp was seen only in HUVECs, and glyceraldehyde-3 phosphate dehydrogenase was detectable in all cell lines tested (FIG. 3B). Hybridization of poly(A) RNA from various human tissues revealed a constitutive expression of ESM-1 in the lung (FIG. 4), whereas lower levels were detected in kidney. The major band detected was found to be similar in size to that in HUVECs (2.2 kb). In addition, no ESM-1 MRNA was detectable in the heart, pancreas, placenta, brain, striated muscle, or liver, even after a 2 week exposure. To determine the endothelial cell origin of ESM-1 in the human lung, we performed in situ hybridization with an $^{35}S$-labeled antisense probe revealed a strong signal exclusively localized on the vacular capillary network within alveolar walls. Capillary veinules and arteriolae were both positive. Vessels of high size were also positive.

Example 3

The ESM-1 Gene in Humans and in Other Species

A Southern Blot of genomic DNA from humans and other species (Zooblot, Clontech) was probed with a Hindlll-digested ESM-1 fragment, which includes 1176 nucleotides at the 5' end, and washed at low stringency. Two major bands were revealed in human DNA with apparent sizes of 6.2 and 5.5 kb (FIG. 5). Two bands of similar intensity were also shown in monkey DNA. Their sizes were slightly greater than those in human DNA (6.7 and 6 kb). In addition, three bands at 8.2, 4, and 3.2 kb were seen in mouse; three bands at 5.5, 4, and 3.4 kb were seen in dog; and one band each, at 5.1, 2.7 and 2.4 kb, was also seen in rat, cow, and rabbit, respectively. By contrast, no band was detected in chicken and yeast DNA. These data suggest that a single gene encodes ESM-1 and indicate the existence of a highly conserved ESM-1 gene between humans and primate and a related gene in other mammalian species.

Example 4

ESM-1 Protein Expression

A 14 kDa COOH-terminal part of the ESM-1 protein was expressed as a fusion protein to glutathione S-transferase in E. coli (FIG. 6A). This protein was further purified as described in ("Materials and Methods" and analyzed by SDS-PAGE and Coomassie Blue staining (FIG. 6B). A polyclonal rabbit immune serum, raised against this product, was first assayed by immunoblotting. A 20 kDa protein was detected only in the supernatants from Sf9 cells infected by ESM-1 recombinant baculovirus (FIG. 6C, lane 4), consistent with the presence of a 20 kDa protein in these cell supernatants metabolically labeled with [$^{35}S$] methionine (FIG. 6C, lane 2). This was confirmed by the immunoprecipitation studies. To localize the ESM-1 protein in COS cells, ESM-1 and mock transfectants were metabolically labeled. A protein with an apparent molecular mass of 20 kDa was immunoprecipitated only in supernatants from COS cells expressing ESM-1 (FIG. 6D, lane 2). A similar band was also found in COS cell lysates transfected with ESM-1. Absence of reducing agents in SDS-PAGE sample buffer had no effects on the mobility of ESM-1 in SDS-PAGE; under both conditions, ESM-1 migrated at 20 kDa, indicating that there are no disulfide-linked ESM-1 oligomers. To identify the presence of ESM-1 in HUVECs, we have performed Western Blots of HUVEC lysates. A 20 kDa band was revealed with the anti-ESM-1 rabbit immune serum (FIG. 7B). This band appeared to be specific to HUVEC's because no such band was seen in several other human cell line lysates including MO7, Daudi, HL60, and Jurkat. This 20 kDa band was further immunoprecipitated in supernatants and lysates from metabolically labeled HUVECs, giving similar results as ESM-1 transfected COS cell immunoprecipitation (FIG. 7A). Thus, the identical sizes of ESM-1 in HUVECs and in COS cells transfected with ESM-1 strongly indicate that the coding region of the ESM-1 cDNA is full length and the reading frame is correct.

Example 5

Modulation of ESM-1 Expression by Cytokines

To determine the action of cytokines on ESM-1 expression, HUVECs were first treated with TNFα, and ESM-1 mRNA levels were examined by Northern Blot. An up-regulation of ESM-1 mRNA was observed; it was time-dependent, peaking at 18 h after addition of TNFα (FIG. 8). The magnitude of this up-regulation was 3–4 fold the level of untreated cells and was constantly observed in five separate experiments. An early and transient down-regulation of ESM-1 mRNA could also be observed in three out of the five experiments, starting at 15 min and persisting up to 1 h 30 min after addition of TNFα (FIG. 8). To control the efficiency of the cytokine activation, these blots were reprobed with an E-selectin-specific DNA probe. A single 3.9 kb band corresponding to the E-selectin mRNA was shown to be rapidly and transiently up-regulated, peaking at the third hour after addition of TNFα (FIG. 8). Ethidium bromide gel staining and β-actin probing as controls confirmed that equal amounts of total RNA were present in each lane. HUVECs were also treated with IL-1β, IL-4, and IFNY. A pattern of regulation similar to that obtained with TNFα was seen with IL-1β. By contrast, no such change in ESM-1 mRNA level was observed with IL-4 and IFNY, despite a time dependent up regulation of vascular cell adhesion molecule-1 and lCAM-1 mRNA levels (FIG. 9). Unexpectedly, when combined with TNFα, IFNY, but not IL-4, clearly inhibited TNFα-induced ESM-1 mRNA levels (FIG. 9). By contrast, IFNY and TNF-α displayed a synergistic induction of lCAM-1 gene expression.

These data suggest that the expression of the ESM-1 gene is not only constitutive, but also is under the control of several cytokines.

Example 6

Inhibition of lCAM-1 function

Materials and Methods

Materials

All the culture media and the fetal calf serum were purchased from Gibco BRL. The cell lines were provided from the ATCC and from C. Lagrou (Institut de Biologie de Lille, PR. D. Stehelin, Lille), except for the Sl-B-1 cell line, which was a gift from Dr. G. Klein (Karolinska Institute, Stockholm, Sweden).

SKW 6.4 and Sl-B-l1 cell lines were cultured in RPMl 1640 containing 10% heat inactivated fetal calf serum. The cells were washed in Hank's balanced salt solution (HBSS, Gibco BRL) 2 times and resuspended in HBSS at $10^7$ cells per ml.

cDNA Construction and Purification

ESM-1 was subcloned in Xhol-digested pCDM8 vector in order to obtain the ESM-1 sens expression vector. Thereafter ESM-1 was subcloned into the pcDNA3© vector. ICAM-1 and E selectin, cloned into the pCDM8 vector, were purchased by British Technology. The VCAM-1 cDNA was amplified. The plasmid DNAs were purified by standard method using silica columns (Qiagen).

Transfection Method 5 to $10\times10^6$ COS cells were transfected with 1 µg purified DNA per $10^6$ COS. The transfection method used 12 µl Lipofectamin© (Gibco BRL) per µg DNA. The protocol was exactly as recommended by the manufacturer. One ml OptiMEM© (Gibco BRL) per $10^6$ COS cells containing the DNA and the Lipofectamin was added to COS cells and incubated 5 hours at 37° C. The COS cell medium was then replaced by fresh complete medium containing DMEM and 10% heat inactivated fetal calf serum and 2 mM L-glutamin. The controls were made of untransfected and mock transfected COS cells. The transfected COS well were then processed as described below.

Leukocyte adhesion to COS Cells

The COS cells were transfected by lCAM-I, lCAM-1+ control pcDNA3 vector, ESM-1, lCAM-1+ESM-1. After 18 hours culture, the transfected COS cells were detached by trypsin and subcultured in 4 chambers culture slides (Nunc) ($2\times10^5$ per well) for another 24 hours at 37° C. One hundred µl of the human cell line suspensions were added to the transfected COS cell cultures and incubated 30 minutes at 37° C. Then, the chamber coverslides were removed. The slides were washed 3 times in HBSS, fixed immediately in PBS containing 0.1% glutaraldehyde for 30 minutes at 4° C. and washed in PBS. The slides were examined by optical microscopy (40×), and the cell forming rosettes onto COS cells were counted optically (only the rosettes containing up to five leukocytes per COS cell were counted). Four fields were counted per well.

lCAM-1 Expression 0.5 to $1\times10^6$ COS cells in 35 mm culture wells were transfected by lCAM-1, lCAM-1+control pcDNA3 vector, ESM-1, ESM-1 +control pcDNA3 vector, lCAM-1+ESM-1, lCAM-1+E selectin, lCAM-1+ESM-1 antisense. After 48 hours culture, the COS cells were washed in HBSS 2 times and lysed in 1 ml PBS containing 0.5% NP40 and anti-proteases (Complete©, Boehringer) for 30 minutes at 4° C. in agitation. The COS cell lysates were then stored at −20° C. The quantitation of lCAM-1 was performed by ELISA (R&D). The results are given in ng per ml.

Cell ELISA on COS cells.

The COS cells were seeded, 24 hours after cotransfection into 96 well microculture plate for another period of 24 hours culture. The cells were then washed 2 times with PBS and fixed with 0.05% glutaraldehyde in PBS for 10 min. at 4° C. The cells were then washed 3 times with PBS and incubated in the saturation buffer containing 0.5 mM EDTA, 0.1% BSA in PBS for 1 hour at 4° C. The cells were washed 3 times and incubated for one hour at room temperature with 0.2 µg of an anti-lCAM-1 mouse monoclonal antibody (Beckton-Dickinson). The cells were washed and incubated with 1:5000 (v:v) of a peroxidase-labeled anti-mouse lgG polyclonal antibody (Institut Pasteur Production). After four additional washings, 100 µl of carbonate/hydrogen carbonate buffer containing $H_2O_2$ and o-phenylene-diamine was added for 30 min, after which, the reaction was stopped with 100 μl 2N H$_2$SO$_4$. Absorbance was read in a multiwell scanning spectrophotometer at 492 nm. All analyses were performed in triplicate. The expression level of lCAM-1 is done as the mean±sd of absorbance of four separate experiments.

Results

Based on the homology between ESM-1 and the human integrin β2, we have hypothetized that ESM-1 might influence the interaction between lCAM-1 and LFA-1. In order to examine this hypothesis, the adhesion of several human cell lines were studied onto COS cells cotransfected with lCAM-1 and ESM-1 cDNAs. The results demonstrated a significant and reproducible inhibition of the lCAM-1 dependent cell adhesion (FIG. 10). Unexpectedly, when the cotransfected cells were washed before the cell adhesion assay, the effect of ESM-1 still occurred. Moreover, when the supernatants from COS-ESM-1 transfectants were pre-incubated with the Sl-B-l and SKW cell lines, no difference in their adhesiveness to lCAM-1 transfected COS cells was observed. Thus, in the COS cell model, ESM-1 appeared to inhibit specifically lCAM-l dependent cell adhesion, primarily via an activity onto lCAM-l function rather than an action on the LFA-1.

The second set of experiments was to quantify the expression of lCAM-1 into COS cells cotransfected with lCAM-1 and ESM-1 cDNAs. The transfected COS cells were lysed and the total lCAM-1 and the ESM-1 contents in these cell lysates were quantified by ELISA. The results demonstrated a significant decrease of lCAM-1 expression which was dependent on the presence of ESM-1.

This inhibition was considered specific since no such an could be found in cotransfection with antisense ESM-1 or E-selectin (FIG. 11). Convergent with the inhibition of the expression if lCAM-1 in COS cell lysate, the expression of lCAM-1 at the cell surface is also decreased (FIG. 12). In another hand, a released form of lCAM-1 has not been detected in the COS cell supernatants.

MATERIALS AND METHODS OF EXAMPLES 7 TO 11

1. Reagents, Cell Lines and Cell Culture.

Anti-CD11a (clone HI111 and clone G43-25B), anti-CD11b (clone ICRF44), anti-CD18 (clone 6.7), anti-CD2 and anti-CD3 mAbs were purchased from Pharmingen. Anti-CD44 mAb was purchased from Sigma. CM5 sensor-chips were from BIAcore. The development of cell lines expressing the wild-type form of ESM-1 (ESM/WT) was previously described (Bechard et al, submitted). ESM/WT was purified sequentially by ion exchange chromatography followed by immunoaffinity chromatography. Lymphoblastic cell lines JURKAT and SiB-1, monocytic cell line U937 and myelomonocytic cell line HL60 were cultured in RPMI-1640 medium, foetal calf serum (FCS) 10% and 2 mM L-glutamine. Monocytic cell line THP1 was cultured in Dulbecco's medium, FCS 10% and 2 mM L-glutamine. 293-ESM, 293-ICAM-1/Fc transfected and established cell lines, which produce soluble ESM-1 and soluble ICAM-1, were cultured in Dulbecco's medium, FCS 10% and 2 mM L-glutamine. Peripheral blood mononuclear cells (PBMC) were obtained from healthy individual volunteers after Ficoll gradient centrifugation (Pharmacia, Uppsala, Sweden). Mononuclear cells were resuspended in RPMI-1640 supplemented with 10% of calf serum, 2 mM L-glutamine and antibiotics.

2. Development of Anti-ESM-1 Monoclonal Antibodies.

In order to obtain anti-ESM-1 mAbs against the cysteine-rich region of ESM-1, the native form, produced by an established CHO-ESM cell line, was purified. Balb/c mice were then immunized (10 microg/mouse) with a standard immunization protocol using Freund adjuvant. The hybridoma cells secreting the anti-ESM-1 mAbs were obtained by fusion, screening and subcloning as previously described (Bechard et al., 2000). Five hybridoma cell clones were obtained and were called MEC (Mouse monoclonal antibody to ESM1 produced by CHO cells). Four of them were of IgGl, k isotype (MEC 4, 5, 15 and 36). One of them was of IgM, k isotype (MEC 11). The hybridoma clones were cultured in serum-free medium and anti-ESM-1 mAbs were purified on protein G-sepharose chromatography (Pharmacia).

3. Flow Cytometry Analysis.

Binding of ESM1 to PBMC and to Jurkat cells was measured by analysis on a FACScalibur (Becton Dickinson). 500,000 cells were incubated with or without 300 ng/mL of purified ESM1 in incubating buffer containing PBS, CaCl2 1 mM, MgCl2 1 mM, MnCl2 1 mM and in some experiments EDTA 5 mM for 1 h at 4° C. Cells were washed 3 times in incubating buffer. Bound ESM1 was revealed by an incubation with an anti-ESM1 mAb MEC 15 versus an isotype-matched mouse IgG1 as a negative control, for 30 min at 4° C. Cells were washed 3 times in incubating buffer and then incubated with a FITC-anti-mouse IgG at 1/100. Cells were washed 3 times in incubating buffer before FACS analysis.

4. Quantitative Binding Evaluation.

To evaluate the binding of ESM-1 to different leukocytic cell lines, ten millions of cells (Jurkat, SIB-1, THP1, U937 and HL60) were incubated in 2mL of RPMI-1640 medium containing 300 ng/mL of purified ESM-1, for 1 h, at 4° C. Cells were centrifuged at 1,500 rpm for 5 min at 4° C. Cells were washed 3 times in ice-cold buffer without ESM-1 and were lysed at 4° C. in 500 microL of lysis buffer containing: PBS, complete anti-proteases cocktail containing EDTA (Boehringer-Manheim) and NP40 0.5% (Boehringer-Manheim). After removal of insoluble material by centrifugation at 10,000 rpm for 15 min, bound ESM-1 was quantified by a specific ELISA (20). In some experiments the binding temperature was performed in a 37° C. waterbath and washed with preheated incubating medium. Activation was performed by incubation of PMA (100 ng/mL) to 37° C.-preheated cell suspension for various periods of time from 5 to 30 minutes. The tubes were then cooled on ice, incubated with ESM-1 for 1 h at 4° C., and then washed with ice cold incubating medium. To evaluate the divalent-ion dependence of the binding, Jurkat cells were incubated in PBS, containing either 1 mM CaCl2, 1 mM MgCl2 or 1 mM MnCl2, in the presence of 300 ng/mL purified ESM-1 for 1 h at 4° C. Jurkat cells were also incubated in RPMI-1640 medium containing 300 ng/mL of purified ESM-1, with or without EDTA 5 mM, for 1 h at 4° C.

5. Coimmunoprecipitation Procedure.

Fifty millions of Jurkat cells were incubated in 10 mL of RPMI-1640 complemented with purified ESM-1 at the concentration of 300 ng/mL and MgCl2, MnCl2 and CaCl2 at 1 mM for 1 h at 4° C. Then, cells were washed 3 times in ice-cold RPMI-1640 medium and were lysed in 500 microL of a specific lysis buffer (PBS, EDTA free complete anti-proteases cocktail (Boehringer-Manheim), 1 mM MgCl2, 1 mM MnCl2, 1 mM CaCl2, and octylthioglucoside 5 mM (Boehringer-Manheim), for 30 min at 4° C. After removal insoluble material by centrifugation at 10,000 rpm at 4° C., supernatants were incubated with 6 micrograms of different mouse monoclonal antibodies at 4° C. After 2 h, 150 microL of anti-mouse Fc agarose beads were added during 1 h at 4°

C. Then, beads were washed three times in lysis buffer by centrifugation at 2,500 rpm at 4° C. Next, beads were eluted with 200 microL of MgCl2 3M for 10 min at room temperature. After rapid centrifugation, 200 microL of eluate were resuspended with 3 mL of PBS containing 1 tablet of complete anti-proteases cocktail. Eluate was desalted and was concentrated on 30 kD centricon (Amicon). ESM-1 was quantified by a specific ELISA.

6. Real-Time Bimolecular Interaction Assay.

The BIAcore system (Pharmacia Biosensor AB, Uppsala, Sweden) was used. In this system, binding of soluble ligands to immobilized ligands was measured in arbitrary units (RU). There was a linear relationship between the mass of the protein bound to the immobilized protein and the RU observed (1000 RU=1 ng/mm2 bound protein). An anti-CD11a (HI111) mouse monoclonal antibody was immobilized at 8000 RU to the carboxymethylated dextran matrix of the sensor chip according to the manufacturer's protocol using the Amine Coupling Kit (BIAcore AB), and compared with a control surface (activated and blocked sensor surface). LFA-1 molecules from the Jurkat lysates could only be fixed by immuno-affinity procedure. 200 millions of Jurkat cells were lysed in 2 mL of lysis buffer (PBS, 1 mM MgCl2, 1 mM MnCl2, complete anti-proteases cocktail EDTA-free and 5 mM octylthioglucoside) for 30 min at 4° C. After removal of insoluble material by centrifugation and incubation in a sonication bath, the lysate was injected at a flow rate of 5 microL/min for 30 min at 25° C. in order to immobilize approximatively 1500 RU of LFA-1 molecules. Next, CD11a mAb (G43-25B), CD18 mAb and purified ESM-1 were diluted in running buffer (PBS, 1 mM MgCl2, 1 mM MnCl2) and injected at a flow rate of 5 microL/min for 5 min at 25° C. The association rate constant (ka) and the dissociation rate constant (kd) were fitted calculated according to the BIAevaluation software version 3.1 provided by the manufacturer. The affinity constant was calculated from the equation Kd=kd/ka.

7. Metabolic Radioisotope Labeling of Soluble ICAM-1/Fc

A form of an ICAM-1/Fc chimeric protein consisting of the three first extracellular domains of ICAM-1 fused to the Fc fragment of human IgG1 was expressed in 293 cells as previously described (Bechard et al., 2000). Exponentially growing adherent cultures (293-ICAM-1/Fc cells) were washed twice in a methionine and cysteine-free Eagle's medium dulbecco containing 5% dialysed FCS, and were incubated in this medium for 2 h at 37° C. The medium was then changed to methionine and cysteine-free Eagle's medium; dulbecco supplemented with 35S methionine (50 mCi/mL of medium 35S Trans-label, 1175 Ci/mmol, ICN) overnight at 37° C. Supernatants were cleared by centrifugation at 2000 rpm for 5 min and were loaded on an anti-human Fc-agarose column according to the manufacturer's recommendations (Biorad). Soluble ICAM-1 was eluted in MgCl2 3M, desalted and concentrated on 30 kDa centricon. Concentration of soluble ICAM-1 was determined by a specific soluble ICAM-1 ELISA, and a ratio amount/cpm was obtained and the specific activity was around 75000 cpm/microgram.

8. Analysis of the Binding of Soluble ICAM-1/Fc to the Jurkat Cells.

Jurkat cells were incubated in RPMI-1640 medium supplemented or not with ESM-1 at a concentration of 300 ng/mL, for 1 h at 4° C. Cells were washed twice in RPMI-1640 medium and incubated in medium supplemented with radiolabeled soluble ICAM-1/Fc (1 microg/mL) for 30 min either at 4° C. or at 37° C. Cells were washed twice with medium heated at corresponding temperatures and resuspended in 2 mL of liquid of scintillation. Binding of soluble ICAM-1/Fc was evaluated by cpm counting in a Beckman counter. To determine the optimal effect of ESM-1, some experiments were conducted with various concentrations of ESM-1 from 1 ng to 1 $\mu$g incubated with Jurkat cells prior to ICAM-1/Fc binding.

Example 7

Binding of Extracellular ESM-1 to the Cell-Surface of PBMC and of Jurkat Cells

To study the possibility that ESM-1 may interact with PBMC obtained from healthy volunteers, we explored the binding ability of ESM-1 to PBMC by flow cytometry analysis. When human PBMC were incubated with ESM-1, a consistent and specific binding to the cell-surface of human lymphocytes (MFI=12.07+/−2.3) was observed as compared to the cells not incubated with ESM-1 (MFI= 4.12+/−0.9). In addition, human monocytes also bound ESM/WT (MFI=25.59+/−3.6) as compared to control monocytes (MFI=14.78+/−1.3) (FIG. 13A). To better characterize the cell surface binding of ESM-1, several cell lines (Jurkat and SIB-1 lymphoblastoid, U937 and THP1 monocytoid, and HL60 myeloid cell line) were examined for their ability to bind ESM-1 (FIG. 13A). As shown in FIG. 13B, ESM-1 bound to the cell surface of Jurkat cells (MFI=7.51+/−0.8) as compared to Jurkat cells not incubated with ESM-1 (MFI= 2.22±0.5). SIB-1 cells, a B lymphoblastoid cell line also bound ESM-1 to a similar extent than Jurkat cells. By contrast, U937, THP1, and HL60 cells did not show any significant ESM-1 binding (data not shown). In order to quantify ESM-1 present on the cell surface, bound ESM-1 was released by complete cell lysis and was evaluated by a specific ELISA. In a resting state, only Jurkat and SIB-1 lymphoblastoid cell lines were able to bind constitutively and significantly ESM-1 (FIG. 14). The Jurkat cells bound approximately 2.75 ng for ten millions of cells, which was less than the binding of ESM-1 to the SIB-1 cells (3.7 ng for ten millions of cells). It is unlikely that the ESM-1 level in cell lysates was related to an endocytic form of ESM-1 because all the experiments were performed on ice. On the other hand, no ESM-1 nor related forms could be detected by RT-PCR and specific ELISA, discarding any endogenous synthesis and expression of ESM-1 by Jurkat and SIB-1 cells. The ESM-1 level in cell lysates was in agreement with the MFI, clearly indicating that ESM-1 in cell lysates reflected the cell surface bound ESM-1. In contrast, U937, THP1 and HL60 cells did not bind ESM-1 constitutively. Consequently, ESM-1 was shown to bind to the human normal and established lines of leukocytes indicating the putative existence of a specific receptor for ESM-1 at their surface.

Example 8

Characteristics of the Binding of Extracellular ESM-1 on Jurkat Cells

In order to characterize the role of divalent ions on the binding of ESM-1 to Jurkat cells, we first examined the effect of EDTA. We found initially that the binding of ESM-1 to Jurkat cells was completely abolished by the presence of EDTA in the medium (FIG. 13B and 16A). Incubation of purified ESM-1 with Jurkat cells in PBS did not lead to ESM-1 binding. Moreover, the single addition of either $Ca^{2+}$, $Mg^{2+}$ or $Mn^{2+}$ ions in PBS medium could restore the binding activity of ESM-1 to Jurkat cells in a similar fashion for each of the divalent ions (FIG. 16B). In order to determine if the putative divalent ion-dependent binding site on the surface of Jurkat cells was saturable, dose-response curves of bound ESM-1 were performed in the presence or in the absence of EDTA. Substraction of bound ESM1 in the presence of EDTA from that in the absence of EDTA gave bound ESM-1 that is divalent ion-dependent. This resulting curve demonstrated that bound ESM-1 reached a plateau beginning at 4 nM (FIG. 16C). Such experiments conducted with $2\times10^7$ and $5\times10^7$ cells per point gave curves with a quite similar plateau. These results were in clear agreement with the presence of a divalent ion-dependent and saturable binding site for ESM-1 on the surface of Jurkat cells.

Figure 15:
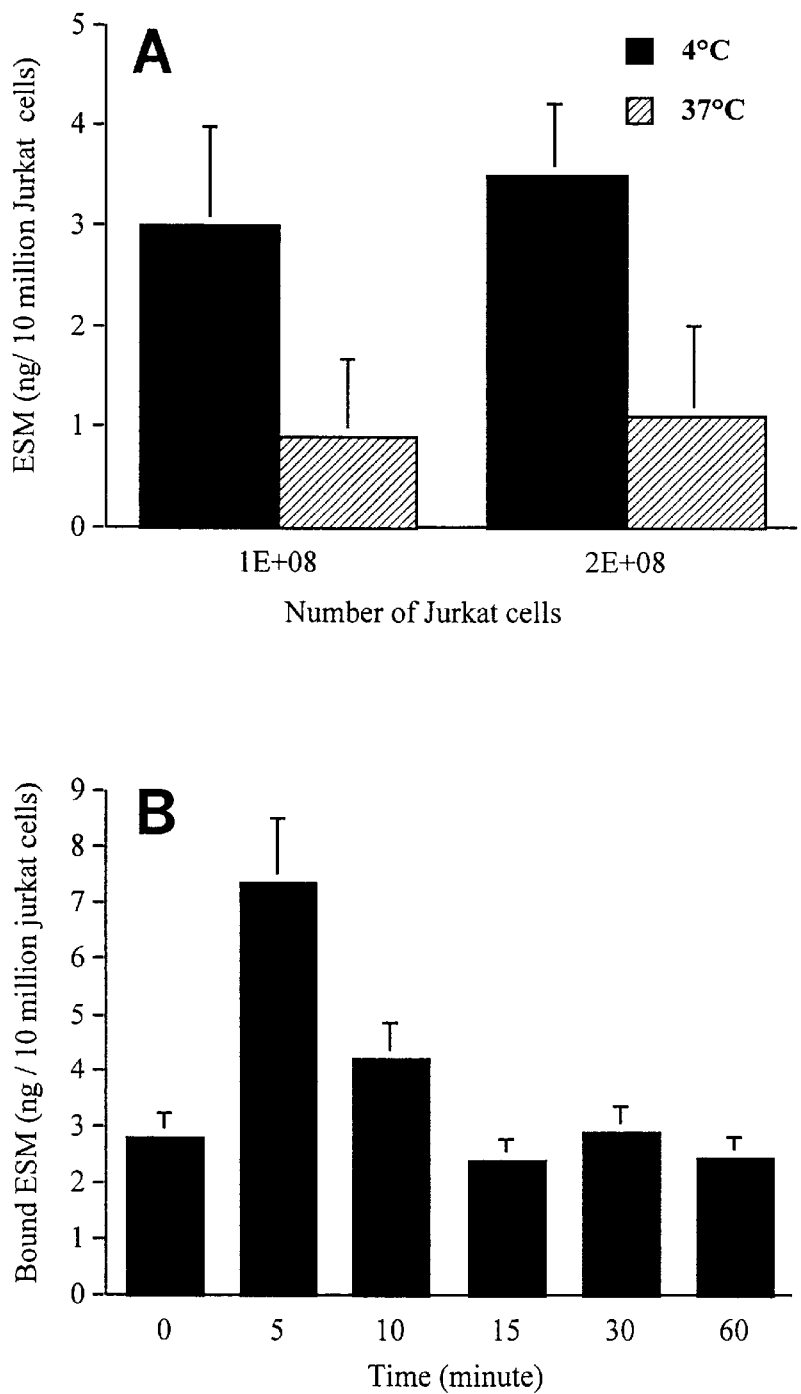

The effect of temperature on ESM-1 binding to the Jurkat cells was next examined. The results are depicted in FIG. 15. The binding of ESM-1 at 37° C. still persisted but in lower extend than at 4° C. Identical results were obtained whatever the cell number. Near half quantity of bound ESM-1 was lost by shifting the binding temperature from 4° C. to 37° C., indicating that membrane fluidity or metabolic energy are involved in the dissociation of bound ESM-1 from Jurkat cells. To appreciate a possible modulation of ESM-1 binding activity by Jurkat cells, these were activated non specifically by PMA. The time course kinetic of activation showed a rapid increase till 5 min incubation with PMA. This increase was also found transient, with a normalization of the ESM-1 binding after 15 min activation, arguing for the presence, at the surface of Jurkat cells, of a regulated binding site for ESM-1.

Example 9

Effect of an Anti-LFA-1 Monoclonal Antibody on the Binding of Extracellular ESM1 to Jurkat Cells To identify the binding site of ESM-1, we focused on the beta 2 integrins because of some aminoacid sequence homology between ESM-1 and the cysteine-rich region of CD18 (Lasalle et al., 1996). This led us to the speculative hypothesis that ESM-1 might bind to the a chains of beta 2 integrins that appeared as the most interesting candidate because they were expressed on both PBMC and Jurkat cells. Thus, coimmunoprecipitation experiments were carried out with different anti-CD11a and anti-CD18 mAbs. It was observed that bound ESM-1 could reproducibly be immunoprecipitated from Jurkat cells by an anti-ESM-1 mAb clone MEC15 (positive control) (14.1+/−3.2 ng/mL) and interestingly could be also coimmunoprecipitated by an anti-CD11a mAb clone HI111 (4.8+/−0.8 ng/mL) and by an anti-CD18 mAb (4.6+/−1.1 ng/mL) (FIG. 17A). On the contrary, ESM-1 could not be coimmunoprecipitated by anti-CD44, anti-CD3 and anti-CD2 mAbs despite their expression at the surface of Jurkat cells, as checked by FACS analysis. However, anti-CD11a mAbs were differentially able to coimmunoprecipitate bound ESM-1. The blocking anti-CD11a (clone HI111), which was known to inhibit the binding of ICAM-1, coimmunoprecipitated ESM-1, while the non blocking anti-CD11a (clone G43-25B) was inefficient despite similar MFIs obtained with both mAbs by FACS. To test in vitro whether anti-CD11a mAbs could modify the binding of ESM-1 to Jurkat cells, Jurkat cells were preincubated with different mAbs and then subjected to ESM-1 binding analysis. Surprisingly, as shown in FIG. 17B, the anti-CD11a mAb (clone HI111), in the presence of divalent ions, led to a consistent increase of ESM-1 binding (17.2+/−1.5 ng/mL), as compared to controls: in absence of specific mAb (5.8±0.3 ng/mL) and with an isotype-matched control mAb (6.1±0.5 ng/mL). These results demonstrate a physical association between ESM-1 and LFA-1 and that the binding of ESM-1 may be regulated by a specific anti-CD11a mAb clone HI11.

Example 10

Real-Time Interaction Between LFA-1 and Extracellular ESM-1

To better define the interaction between LFA-1 and ESM-1, a real-time observation by BIAcore analysis was carried out. Sensor chip was filled with detergent lysates of Jurkat cells in order to capture functional LFA-1 molecules. Specific binding of the heterodimeric form of LFA-1 to the anti-CD11a mAb coupled censorship was observed. In this assay, anti-CD11a mAb (HI111) was immobilized on the surface of the carboxymethyl 5 sensor chip as described in Materials and Methods. The binding of heterodimeric LFA-1 to mAb coated chip was consistently detected. The presence of both CD11a chain and CD18 chain was checked by injecting either another anti-CD11a mAb (G43-25B), or an anti-CD18 mAb in the LFA-1 captured channel. As reported in FIG. 18A, LFA-1 was strongly captured under its heterodimeric form, which was essential to keep functionality of LFA-1. Next, we have also examined the interaction of LFA-1 and purified human ESM-1 by BIAcore biosensor. In this type of assay, immunoaffinity coupled LFA-1 was immobilized on the sensor chip surface as previously described. Before LFA-1 was immobilized on the surface of the sensor chip, a control experiment was preformed in which purified ESM-1 was injected on the mAb coated surface or activated and desactivated surface. No interaction was detected between the mAb coated surface or control surface and ESM-1 at the highest concentration used in this experiment (data not shown). Purified ESM-1 was then injected at indicated concentrations to the LFA-1 captured surface, and the response (in resonance units) versus time (in seconds) was recorded. An overlay of sensor-grams for the binding of ESM-1 to LFA-1 is shown in FIG. 18B. Sensor-grams showed two phases: a fast association phase, detected when purified human ESM-1 was injected and was allowed to bind to the immobilized LFA-1 (0–250 seconds), and a slow dissociation phase, in which the ESM-1 solution was replaced with running buffer (250 to 600 seconds). The association and dissociation phases were fitted and linearized according to the BIAevaluation software 3.1. The association rate constant (ka) calculated from 5 distinct concentrations (from 50 to 300 nM) was $4.41*10^4$ M-1s-1 and the dissociation rate constant (kd) calculated was $8.25*10^{-4}$ s-1. Then, the equilibrium dissociation constant (Kd), calculated from the ratio of the rate constants, was $18.7*10^{-9}$ M.

Example 11

Inhibition of Soluble ICAM-1 to Jurkat Cells Extracellular ESM-1

The fact that ESM-1 has been shown to interact with LFA-1 suggested that ESM-1 might have consequences on the LFA-1/ICAM-1 interactions. In order to explore this hypothesis, metabolically labeled and affinity-purified 3D-ICAM-1/Fc (soluble ICAM-1) was used to examine the effects of ESM-1 on the LFA-1/ICAM-1 interactions. The specific bound ICAM-1 to Jurkat cells (4652±156 cpm) was strongly inhibited by the blocking anti-CD11a mAb clone HI111 (837±168 cpm), indicating that in our experimental model, almost all the labeled ICAM-1 was bound to LFA-1 (FIG. 6A). When ESM-1 was coincubated with soluble ICAM-1 and the Jurkat cells, we observed an inhibition of specific binding of soluble ICAM-1 of 64%+10% (2200 cpm±139 cpm). This inhibitory effect appeared dose-dependent, reaching to a plateau at 300 ng/mL (FIG. 6B). A reduced binding of radiolabeled ICAM-1/Fc on Jurkat cells was observed at 37° C. (1419±165 cpm), however, ESM-1 still persisted to inhibit ICAM-1 binding in a level similar to the neutralizing CD11a mAb (772±88 cpm ; 46±9% ; FIG. 19A). In addition, the ability of soluble ICAM-1 to inhibit the binding of ESM-1 to Jurkat cells was also explored. The preincubation of Jurkat cells with 3D-ICAM-1/Fc decreased the binding of ESM-1 of 65% (2.9±0.3 ng/mL), as compared to control (7.2±0.4 ng/mL). However, the 3D-ICAM-1/Fc pretreatment with neutralizing anti-ICAM-1 mAb totally restored the binding of ESM-1 to Jurkat cells (6.7±0.6 ng/mL) (FIG. 20). It is unlikely that ESM-1 had the capacity to bind to the soluble 3D-ICAM-1/Fc while ESM-1 could not be coprecipitated by 3D-ICAM-1/Fc. Thus, these data demonstrate that ESM-1 and ICAM-1 can compete for the binding to the LFA-1 counter receptor and consequently ESM-1might modulate the LFA-1 and ICAM-1 dependent function.

Materials and Methods for Examples 12 to 13

Subjects

The study was conducted in the intensive care units of the University Hospital of Geneva, Switzerland, and of the University Hospital of Lille (France). Four groups of subjects were prospectively studied, one group of healthy non-atopic subjects (sex ratio: 1) and three groups of pulmonary and/or systemic septic inflammatory disorders (SR: 1.6, age: 56±2 years) (Table 1). All non-atopic healthy volunteers from the Department had negative standard skin prick-tests, and no clinical history of allergy. Dr. A. Tsicopoulos (U416 INSERM) kindly provided serum samples from healthy allergic subjects undergoing Hymenopterous venom desensibilisation. None of the 68 patients were receiving corticosteroids or undergoing hemodialysis at the moment of the blood sampling. The protocol was approved by the local ethical committee of the University Hospitals.

Definitions

The following terms were used in the study.
Infection is a microbial phenomenon characterized by an inflammatory response to the presence of micro-organisms or the invasion of normally sterile host tissues by these organisms. Systemic inflammatory response syndrome (SIRS) with no signs of infection, is characterized by the presence of at least two of the following four clinical criteria: a) fever or hypothermia (temperature>100.4° F. [>38° C.] or <96.8° F. [<36° C.]); b) tachycardia (>90 beats/min); c) tachypnea (>20 breaths/min or $PaCO_2$<4.3 kPa [32 mm Hg]); and d) an altered white blood cell count of >12,000 cells/mm$^3$, <4,000 cells/mm$^3$, or the presence of >10% band forms, respectively.
Sepsis is defined as SIRS with an infection. Severe sepsis is defined as a sepsis associated with organ dysfunction, hypoperfusion or hypotension. Hypoperfusion and perfusion abnormalities may include, but are not limited to oliguria (output of <30 mL/hr), lactic acidosis (serum lactate level of >2 mmol/L) or an acute alteration in mental status without sedation (a reduction by >=3 points from baseline value in the Glasgow coma score).
Septic shock is defined as the presence of sepsis accompanied by a sustained decrease in systolic blood pressure (<90 mm Hg, or a drop of 40 mm Hg from baseline systolic blood pressure), along with the presence of perfusion abnormalities (see above), despite fluid resuscitation and the need for vasoactive amines to maintain adequate blood pressure (American College of Chest Physicians/ Society of Critical Care Medicine Consensus Conference., 1992).

Study Design

For each patient, following clinical and biological details were obtained at the hospital entrance: age, sex, main and secondary diagnosis according to the American College of Chest Physicians and the Society of Critical Care Medicine Consensus Conference (1992), antecedents, treatment, life status ten days after the blood sampling, plasma and serum ESM-1 concentrations. For most of the patients, blood biological parameters as circulating soluble ICAM-1 (sICAM-1), procalcitonin (proCT), and C-reactive protein (CRP) were measured too. Blood samples were collected from each patient (or from each healthy volunteer) in dry and EDTA tubes, and then spun down 30 minutes at 3500 tr/m (Jouan C3i, France). Serum and plasma respectively obtained were shortly kept at −20° C. before assays. The period of ten days for survival was chosen on the assumption that the infection contributed directly to death in these patients or that contribution of the initial inflammatory disorder to death of any other cause could not be excluded.

ESM-1 Immunoassay

Serum and plasma ESM-1 assays were performed in Lille Pasteur Institute (INSERM U416) by a sandwich-type ELISA as previously described with minor modifications (Bechard et al., 200). Purified monoclonal antibody against ESM-1 (clone MEP14, IgG2a/kappa, produced in the laboratory, (Bechard et al., 2000) was diluted at 5 μg per ml in carbonate buffer 0.1M, pH 9.5, and adsorbed for one night at +4° C. on a 96 well-plate (E.I.A./R.I.A. plate, COSTAR, Cambridge, Mass., USA). The plate was saturated for 1 hour at room temperature with 200 μl by well of PBS containing 0.1% bovine serum albumin and 5 mM EDTA, then washed two times with ELISA buffer (the above buffer plus 0.1% tween 20). A scale was realized with purified ESM-1 (Bechard et al., 2000). The blood samples were serial diluted (1:2 to 1:128), in ELISA buffer and incubated on ELISA plate for one hour at room temperature. The wells were washed three times with ELISA buffer then incubated 1 hour at room temperature with a second monoclonal antibody against ESM-1 (MEC15, clone IgG1/kappa, produced in the laboratory) at 0.1 μg/ml in 100 μl buffer by well. After three washings, a biotinylated anti-mouse IgG1 rat monoclonal antibody (Pharmingen) diluted in ELISA buffer was added for another period of 1 hour, then washed 3 times again, and incubated with 1:10,000 (v/v) Streptavidin peroxidase conjugated (Zymed), washed once again three times with ELISA buffer and two >times with PBS. The peroxidase conjugate was revealed with the TMB substrate (SIGMA, St. Louis, Mo., USA)+25 µl of H202 for 30 minutes. The reaction was finally stopped by addition of 100 µl H2SO4 2N. The plate was read by a spectrophotometer (Anthos Labtec LP40, France) at 405 nm. Plasma or serum ESM-1 concentration was calculated from the optical density and expressed in ng/ml.

Other Blood Markers Assays

Serum sICAM-1 quantitative assay was performed in Lille Pasteur Institute (INSERM U416) by an ELISA assay (Diaclone Research, Besancon, France). The plate was read by a spectrophotometer (Anthos Labtec LP40, France) at 450 nm. Serum sICAM-1 concentration was calculated from the optical density and expressed in ng/ml. Our sICAM-1 normal value was 571±168 ng/ml (219–1042; n=77). In two precedent studies, normal values were 208±20 ng/ml (n=9) or 355±41 ng/ml (n=12) (9,10).

Procalcitonin assay was performed using an ILMA immuno-assay (LUMItest, B.R.A.M.S.-Diagnostica GMBH, Germany). Normal value is below 0.5 ng/ml. Value for SIRS are usually between 0.5 and 2 ng/ml. CRP was measured by immuno-nephelometry, normal value is below 10 mg/l (Morley et al., 1982).

Statistical Analysis

Data are expressed as mean value'standard error (SEM). Comparisons of median levels of ESM-1, sICAM-1, procalcitonin and CRP between the different groups were performed using the one-way analysis ANOVA (Bonferroni-Dunn) test, the Kruskal-Wallis test and the Mann-Whitney test. Correlation between the markers values was tested by the Spearman rank test. Correlation between the circulating marker level and the gravity or the outcome of the patient was performed using the one-way analysis ANOVA (Bonferroni-Dunn) test, the Mann-Whitney test, and the Wilcoxon test. In general, a value of $p<0.05$ was deemed significant. Graphs plotted as vertical boxes show the median, the $10^{th}$, $25^{th}$, $75^{th}$ and $90^{th}$ percentiles as vertical boxes with error bars.

Example 12

Correlation Between Plasma and Serum ESM-1 Levels

In an initial trial, the question whether the conditions of blood sampling might affect the ESM-1 level was studied. Comparison of ESM-1 levels in plasma to those in serum from 41 healthy subjects did show strong correlation (r=0.85, p <0.0001). On FIG. 21, as for the control group, no significant difference was observed for a same patient between plasma and serum ESM-1 levels in the first 36 patients of this study. This suggested first that the blood clothing did not modify the ESM-1 level, and second that ESM-1 could be quantified without any difference from either serum or plasma samples. Therefore, only the ESM-1 serum level was used for the rest of the study.

Example 13

Comparison of the Serum Level of Various Blood Markers in Healthy Volunteers and in Patients A comparison of the serum level of ESM-1 and two conventional blood markers of sepsis, namely C-Reactive Protein and Procalcitonin between a control group of healthy volunteers and three groups of patients with increasing symptoms of sepsis was performed as described in the Materials and Methods Section. The results are shown in Table 1 hereunder.

TABLE 1

Serum ESM-1 value showed significant increase in the different groups of septic patients.

| | | Blood Markers | | | |
|---|---|---|---|---|---|
| Group | n | sESM-1 (ng/ml) | sICAM-1 (ng/ml) | CRP (mg/l) | Procalcitonin (ng/ml) |
| Normal value (healthy non atopic) | 20 | 0.7 ± 0.1 | 571 ± 168 | <10 | <0.5 |
| Patients all together | 61 | 5.4 ± 0.8*** | 2510 ± 261*** | 194 ± 21** | 39.8 ± 12.4*** |
| (Pulmonary) Sepsis | 29 | 2.5 ± 0.3*** | 2336 ± 406*** | 126 ± 15*** | 2.0 ± 1.4 |
| Severe sepsis | 12 | 4.5 ± 1.4** | 2696 ± 721* | 292 ± 73** | 23.8 ± 9.2*** |
| Septic shocks | 20 | 10.0 ± 1.8*** | 2661 ± 373*** | 245 ± 29*** | 90.8 ± 29.5*** |

Blood markers values are shown as mean value ± SEM. Significant difference between each patients group and the normal value (healthy non-atopic subjects group):
*p < 0.01; p < 0.001; *p < 0.0001.

Control Group

A mean value of ESM-1 serum level was 0.7±0.4 ng/ml in the healthy subjects (Table 1) versus 1.0±0.1 ng/ml in the healthy atopic group. Although the difference was small, it is found statistically significant (p<0.05). Therefore, the control group referred hereafter to the group of healthy non-atopic subjects, representing most of the general population, and its mean ESM-1 level as the standard normal value.

Patients Groups

Results of circulating markers in the groups of patients are summarized in Table 1 and illustrated by FIGS. 2 and 3A–C. In sera from patients admitted for severe sepsis, sESM-1, sICAM-1, CRP, and proCT were all found highly increased for each group of patients compared to the control group (table 1). These increased levels were statistically significant (p<0.01 or less) for all markers and for all groups of patients except for the procalcitonin in the sepsis group (Table 1, FIG.22 and 23A–C). The gravity of the disease is defined clinically in 3 graduate levels called sepsis, severe sepsis and septic shock groups. In each of these groups the serum ESM-1 levels increased accordingly with the gravity of the disease showing statistically significant positive correlation (p<0.01, n=61). Similar increases were found with serum procalcitonin and CRP levels (respectively p=0.0001, n=34 and p<0.01, n=43). On the other hand, sICAM-1 was increased of about five times the normal value but in similar levels in each group of patients. There was not any value to assess the gravity in this study (n=61).

Example 14

Post-Translational Modifications of the Secreted Form of ESM-1 From Endothelilal Cells and From Established Cell Lines A. MATERIALS and METHODS Cell Cultures and Materials CHO cells were cultured in alpha MEM (Gibco BRL, Life technologies, France) supplemented with 10% foetal calf serum. SV40-transfected human endothelial cells (SV1 cells) (37) were cultured in RPMI 1640, containing 2 mM L-glutamine and 10% foetal calf serum. Human embryonic kidney cells (293 cell line) were cultured in Dulbecco's (DMEM) with 10% foetal calf serum. Human embryonic kidney-cells (293 cell line) used for the test of proliferation were cultured in Dulbecco's Eagle modified medium (Gibco BRL) complemented with insulin 10 mg/ml and transferring 10 mg/ml. Proteinase K and Chondroitinase ABC were purchased from Boehringer Manheim. Chondoitinases B, AC and, C were from Sigma. Human HGF/SF was from R&D and decorin was from Sigma. Anti-ESM-1 monoclonal antibodies were produced and purified as described previously (Bechard et al., in press).

Development of Cell Expressing ESM-1

The full length ESM-1 cDNA was digested, purified and inserted into XhoI-HindIII opened pcDNA3 expression vector (Invitrogen). The construct was transfected in CHO and 293 cell lines with lipofectamin (GibcoBRL), following selection by G418/(1000 mg/ml or 300 mg/ml respectively). Stable transfected cell lines were obtained by limit dilution and the resulting cell lines were called: CHO-ESM and 293-ESM.

Immunoprecipitation, Immunoblot and Sequence

The size of different forms of ESM-1 was determined by immunoprecipitation and western blotting from cell supernatants and cell lysates. Cells were lysed in buffer containing 0,5% NP40, anti-protease cocktail (Boehringer; Mannheim, Germany) in PBS for 30 min at 4° C. in agitation. Then, lysates were centrifuged at 1000 g for 15 min in order to obtain cleared cell lysates. Supernatants were filtrated on 0.22 mm. One mg of ESM-1 mAb (MEP19) or ICAM-1 mAb (clone 164B) was added to the cleared lysates or cell supernatants and incubated overnight at 4° C. with agitation. Fifty microlitres of anti-mouse immunoglobulin conjugated to agarose beads (Sigma) was added at-4° C. for 902 min, centrifuged, and washed twice with lysis buffer and twice with PBS. The beads were resuspended in 20 to 40 ml of SDS-PAGE sample buffer for 5 min, centrifuged, and the supernatants analyzed. Samples were migrated on SDS-PAGE and were blotted onto nitrocellulose membranes according to standard procedures. After a blocking step, the membranes were incubated 1 hour with ESM-1 mAb (MEP14) at 1 $\mu$g/ml, washed and then incubated 1 hour with an anti-mouse Fc HRP-conjugated secondary antibody (Sigma) followed by washed and developped using an ECL detection kit (Amersham).

For aminoacid sequence analysis, purified ESM-14 was run on SDS-PAGE, electroblotted to a polyvinylidene difluoride (PVDF) membrane (Millipore) and stained withy 0.1% Coomassie blue. The prote in band of 50 kiD was excised from the membrane and the N-terminal sequence was determined by automated Edman degradation on a ABI 473A protein sequencer.

B. RESULTS

In order to determine if ESM-1 was processed as a secretary molecule as suggested by the predicted N-terminal amino acid sequence, ESM-1 was purified from the 293-ESM cell line. The N-terminal sequence of the 50 kD form indicated that the signal peptide of 19 amino acids was cleaved at the predicted site, leading to a mature ESM-1 polypeptide of 165 amino acids beginning at W20 (wsSNNYAVD-P) (SEQ ID NO: 6).

ESM-1 was immunoprecipitated from cell supernatants of HUVEC, SV1, 293-ESM and CHO-ESM cells and then analyzed by Western-blot. In the HUVEC supernatants, we have previously shown that ESM-1 migrates as a diffuse band at about 50 kD. A band similar in size was also observed in the supernatants of SV1 cells, 293-ESM cells and CHO-ESM cells (FIG. 24A). The molecular weight, higher than the predicted size suggested that the secreted form of ESM-1 was post-translationally modified. The fact that purified ESM-1 was better stained on SDS-PAGE with Alcian-blue than with Coomassie-blue suggested that ESM-1 was rather glycosylated (FIGS. 24B, C) than oligomerized through disulphide bonds because reducing conditions did not change the apparent molecular weight of ESM-1.

ADDITIONAL REFERENCES

ASUSBEL ET AL., 1989. CURRENT PROTOCALS IN MOLECULAR Biology, Green Publishing Associates and Wiley Interscience, N.Y.

Bechard, D., V. Meignin, A. Scherpereel, S. Oudin, G. Kervoaze, P. Bertheau, A. Janin, A. B. Tonnel, and P. Lassalle. 2000. Characterization of the secreted form of Endothelial-cell Specific Molecule-1 by specific monoclonal antibodies. *J Vasc Research*, 37(5): 417–425.

FRECHNEY (ed.), 1986. *Immobilized Cells And Enzymes*, IRL Press.

GLOVER (ed.), 1985. *DNA Cloning: A Practical Approach, Volumes I and II Oligonucleotide Synthesis*, MRL Press, Ltd., Oxford, U.K.

GAIT (ed.), 1984. *Nucleic Acid Hybridization*.

HAMES BD AND HIGGINS SJ, 1985. *Nucleic acid hybridization: a practical approach*, Hames and Higgins Ed., IRL Press, Oxford.

Lassalle, P., S. Molet, A. Janin, J. V. Heyden, J. Tavernier, W. Fiers, R. Devos, and A. B. Tonnel. 1996. ESM-1 is a novel human endothelial cell-specific molecule expressed in lung and regulated by cytokines. *J Biol Chem* 271:20458–64.

American College of Chest Physicians/ Society of Critical Care Medicine Consensus Conference. Definitions for sepsis and multiple organ failure, and guidelines for the use of innovative therapies in sepsis. *Crit Care Med* 1992, 20:864–874.

Morley J. J. and Kushner I. Serum C-reactive protein levels in disease. *Ann. N.Y. Acad. Sci.* 1982, 389:406–418.

NEEDLEMAN AND WUNSCH (1972) J. Mol. Biol. 48:442

PERBAL, 1984. *A Practical Guide To Molecular Cloning.*

SAMBROOK, J. FRITSCH, E. F., and T. MANIATIS, 1989. *Molecular cloning: a laboratory manual.* 2ed. Cold Spring Harbor Laboratory, Cold spring Harbor, N.Y.

PEARSON AND LIPMAN (1988) Proc. Natl. Acad. Sci (USA) 85:2444

SMITH AND WATERMAN (1981) Adv. Appl. Math. 2:482, by the homology alignment algorithm of Needleman and Wunsch (19720) J. Mol. Biol. 48:442

Salomon, B., and J. A. Bluestone. 1998. LFA-1 interaction with ICAM-1 and ICAM-2 regulates Th2 cytokine production. J Immunol 161:5138–42.

Zuckerman, L. A., L. Pullen, and J. Miller. 1998. Functional consequences of costimulation by ICAM-1 on IL-2 gene expression and T cell activation. J Immunol 160:3259–68.

What is claimed is:

1. A purified or isolated protein consisting of the amino acid sequence SEQ ID No. 3.

2. A pharmaceutical composition useful for ting a disease linked to leukocyte migration and comprising a protein of claim 1 in combination with at least one pharmaceutically acceptable carrier.

* * * * *

UNITED STATES PATENT AND TRADEMARK OFFICE
CERTIFICATE OF CORRECTION

PATENT NO. : 6,670,328 B1 Page 1 of 1
DATED : December 30, 2003
INVENTOR(S) : Phillippe Lassalle et al.

It is certified that error appears in the above-identified patent and that said Letters Patent is hereby corrected as shown below:

Column 43,
Line 31, "ting" should read -- treating --.

Signed and Sealed this

Twenty-seventh Day of April, 2004

JON W. DUDAS
*Acting Director of the United States Patent and Trademark Office*